US012036177B2

(12) United States Patent
Freeman et al.

(10) Patent No.: US 12,036,177 B2
(45) Date of Patent: *Jul. 16, 2024

(54) SYSTEM FOR ASSISTING RESCUERS IN PERFORMING CARDIO-PULMONARY RESUSCITATION (CPR) ON A PATIENT

(71) Applicant: ZOLL Medical Corporation, Chelmsford, MA (US)

(72) Inventors: Gary A. Freeman, Waltham, MA (US); Jing Pan, Newton, MA (US); Ziad F. Elghazzawi, Newton, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 391 days.

This patent is subject to a terminal disclaimer.

(21) Appl. No.: 17/354,258

(22) Filed: Jun. 22, 2021

(65) Prior Publication Data

US 2022/0000709 A1    Jan. 6, 2022

Related U.S. Application Data

(63) Continuation of application No. 16/270,000, filed on Feb. 7, 2019, now Pat. No. 11,071,685, which is a
(Continued)

(51) Int. Cl.
*A61H 31/00* (2006.01)
*A61B 5/00* (2006.01)
(Continued)

(52) U.S. Cl.
CPC ......... *A61H 31/005* (2013.01); *A61B 5/0059* (2013.01); *A61B 5/02* (2013.01);
(Continued)

(58) Field of Classification Search
CPC .. A61H 31/005; A61N 1/39044; A61B 5/318; A61B 5/0059
(Continued)

(56) References Cited

U.S. PATENT DOCUMENTS 5,431,688 A    7/1995 Freeman
5,683,424 A    11/1997 Brown et al.
(Continued)

FOREIGN PATENT DOCUMENTS

EP    1913923 A1    4/2008
JP    2002517283 A    6/2002
(Continued)

OTHER PUBLICATIONS

International Patent Application PCT/US2012/025358, International Search Report and Written Opinion, dated Nov. 22, 2013.
(Continued)

*Primary Examiner* — Nadia A Mahmood
(74) *Attorney, Agent, or Firm* — The Webb Law Firm

(57) ABSTRACT

A system for assisting a rescuer in performing cardio-pulmonary resuscitation (CPR) on a patient includes: a proximity sensor configured to be positioned at a location corresponding to a location of a rescuer's hand when delivering compressions to a patient's chest, the proximity sensor configured to produce a signal indicative of the rescuer's hands being released from the patient's chest; a medical device operatively coupled with the proximity sensor and configured to provide resuscitative treatment to the patient; and a controller communicatively coupled with the medical device and the proximity sensor. The controller is configured to: determine, based upon the signal from the proximity sensor, if the rescuer's hands have been released from the patient's chest, and trigger an action by the medical device in response to a determination that the rescuer's hands have been released from the patient's chest.

20 Claims, 21 Drawing Sheets

Related U.S. Application Data continuation of application No. 15/833,288, filed on Dec. 6, 2017, now Pat. No. 10,238,574, which is a continuation-in-part of application No. 15/601,465, filed on May 22, 2017, now Pat. No. 10,617,600, which is a continuation of application No. 15/178,578, filed on Jun. 10, 2016, now Pat. No. 9,682,009, said application No. 15/833,288 is a continuation-in-part of application No. 15/175,500, filed on Jun. 7, 2016, now Pat. No. 9,839,576, said application No. 15/178,578 is a continuation of application No. 14/605,653, filed on Jan. 26, 2015, now Pat. No. 9,387,147, said application No. 15/175,500 is a continuation of application No. 14/299,092, filed on Jun. 9, 2014, now Pat. No. 9,364,680, said application No. 14/605,653 is a continuation of application No. 14/107,066, filed on Dec. 16, 2013, now Pat. No. 8,979,764, which is a continuation of application No. 13/555,439, filed on Jul. 23, 2012, now Pat. No. 8,634,937, said application No. 14/299,092 is a continuation of application No. 13/398,280, filed on Feb. 16, 2012, now Pat. No. 8,781,577.

(60) Provisional application No. 61/527,663, filed on Aug. 26, 2011, provisional application No. 61/473,273, filed on Apr. 8, 2011.

(51) Int. Cl.
   *A61B 5/02* (2006.01)
   *A61B 5/0205* (2006.01)
   *A61B 5/11* (2006.01)
   *A61B 5/113* (2006.01)
   *A61B 5/318* (2021.01)
   *A61N 1/39* (2006.01)

(52) U.S. Cl.
   CPC .......... *A61B 5/0205* (2013.01); *A61B 5/1114* (2013.01); *A61B 5/113* (2013.01); *A61B 5/318* (2021.01); *A61B 5/7207* (2013.01); *A61B 5/742* (2013.01); *A61N 1/39* (2013.01); *A61N 1/39044* (2017.08); *A61B 5/6823* (2013.01); *A61N 1/3925* (2013.01)

(58) Field of Classification Search
   USPC .......................................................... 601/41
   See application file for complete search history.

(56) References Cited

U.S. PATENT DOCUMENTS

| | | |
|---|---|---|
| 6,125,299 A | 9/2000 | Groenke et al. |
| 6,213,960 B1 | 4/2001 | Sherman et al. |
| 6,224,562 B1 | 5/2001 | Lurie et al. |
| 6,360,125 B1 | 3/2002 | Weil et al. |
| 6,463,327 B1 | 10/2002 | Lurie et al. |
| 6,865,413 B2 | 3/2005 | Halperin et al. |
| 6,961,612 B2 | 11/2005 | Elghazzawi et al. |
| 7,220,235 B2 | 5/2007 | Geheb et al. |
| 7,220,335 B2 | 5/2007 | Van Gompel et al. |
| 7,565,194 B2 | 7/2009 | Tan et al. |
| 8,010,190 B2 | 8/2011 | Olson et al. |
| 8,034,006 B2 | 10/2011 | Celik-Butler et al. |
| 8,435,193 B2 | 5/2013 | Belalcazar |
| 8,615,295 B2 | 12/2013 | Savage et al. |
| 8,634,937 B2 | 1/2014 | Elghazzawi et al. |
| 8,706,214 B2 | 4/2014 | Tan et al. |
| 8,738,129 B2 | 5/2014 | Packer et al. |
| 8,880,166 B2 | 11/2014 | Tan et al. |
| 8,979,764 B2 | 3/2015 | Elghazzawi et al. |
| 9,364,625 B2 | 6/2016 | Silver et al. |
| 9,387,147 B2 | 7/2016 | Elghazzawi et al. |
| 2003/0208237 A1 | 11/2003 | Locke et al. |
| 2004/0162510 A1 | 8/2004 | Jayne et al. |
| 2004/0172069 A1 | 9/2004 | Hakala |
| 2004/0267325 A1 | 12/2004 | Geheb et al. |
| 2005/0067816 A1 | 3/2005 | Buckman |
| 2005/0119706 A1 | 6/2005 | Ideker et al. |
| 2005/0234515 A1 | 10/2005 | Freeman |
| 2007/0060785 A1 | 3/2007 | Freeman et al. |
| 2007/0276300 A1 | 11/2007 | Olson et al. |
| 2008/0081321 A1 | 4/2008 | Cantrell et al. |
| 2008/0300518 A1 | 12/2008 | Bowes |
| 2008/0312565 A1 | 12/2008 | Celik-Butler et al. |
| 2008/0312708 A1 | 12/2008 | Snyder |
| 2009/0112274 A1 | 4/2009 | Herbert |
| 2010/0022904 A1 | 1/2010 | Centen |
| 2010/0211127 A1 | 8/2010 | Eerden |
| 2010/0222718 A1 | 9/2010 | Freeman et al. |
| 2010/0241181 A1 | 9/2010 | Savage et al. |
| 2011/0040217 A1 | 2/2011 | Centen |
| 2011/0172572 A1 | 7/2011 | Belalcazar |
| 2011/0202100 A1 | 8/2011 | Tan et al. |
| 2011/0284004 A1 | 11/2011 | Silver et al. |
| 2011/0313482 A1 | 12/2011 | Dupelle et al. |
| 2012/0123224 A1 | 5/2012 | Packer et al. |
| 2012/0259156 A1 | 10/2012 | Freeman |
| 2016/0220833 A1 | 8/2016 | Tan et al. |
| 2016/0296418 A1 | 10/2016 | Freeman |
| 2017/0120063 A1 | 5/2017 | Freeman et al. |
| 2017/0225001 A1 | 8/2017 | Zaidi et al. |

FOREIGN PATENT DOCUMENTS

| | | |
|---|---|---|
| JP | 2006263330 A | 10/2006 |
| JP | 2007525050 A | 8/2007 |
| JP | 2010540010 A | 12/2010 |
| WO | 0057955 A1 | 10/2000 |
| WO | 2005021089 A1 | 3/2005 |
| WO | 2005070497 A1 | 8/2005 |
| WO | 2006058133 A2 | 6/2006 |
| WO | 2006104977 A2 | 10/2006 |
| WO | 2010010567 A2 | 1/2010 |

OTHER PUBLICATIONS

International Patent Application PCT/US2012/047836, International Search Report and Written Opinion, dated Oct. 12, 2012.

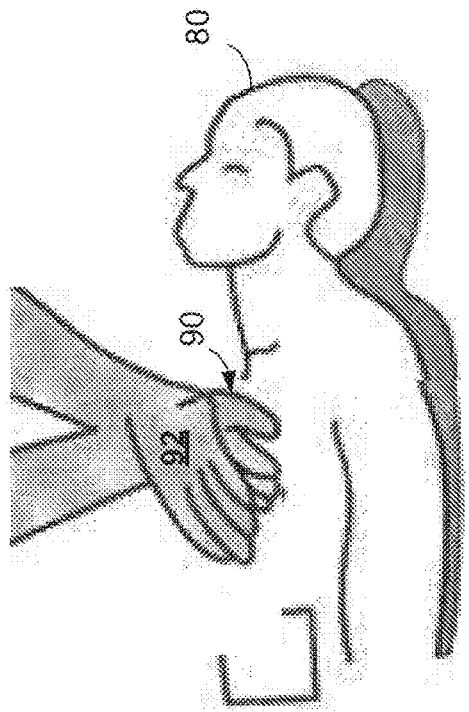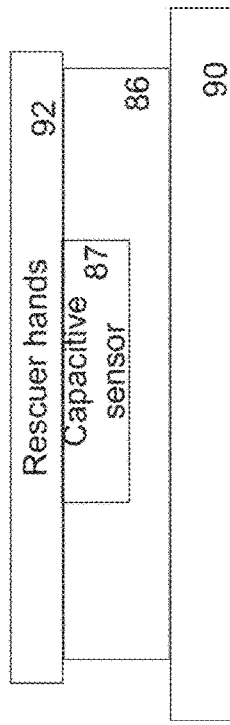
FIG. 9A
FIG. 10A
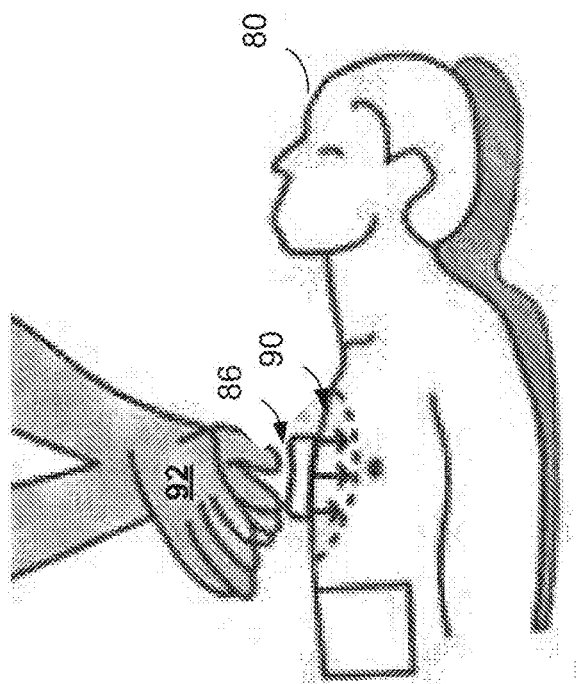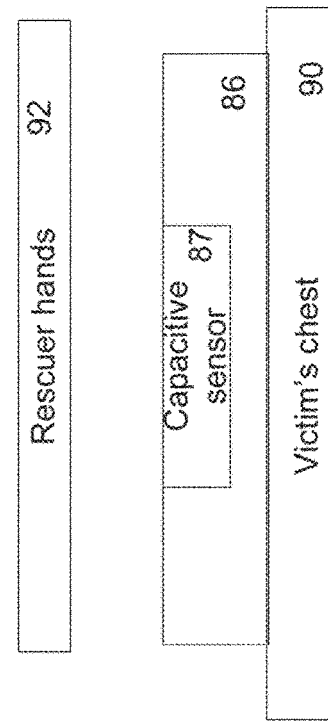
FIG. 9B
FIG. 10B

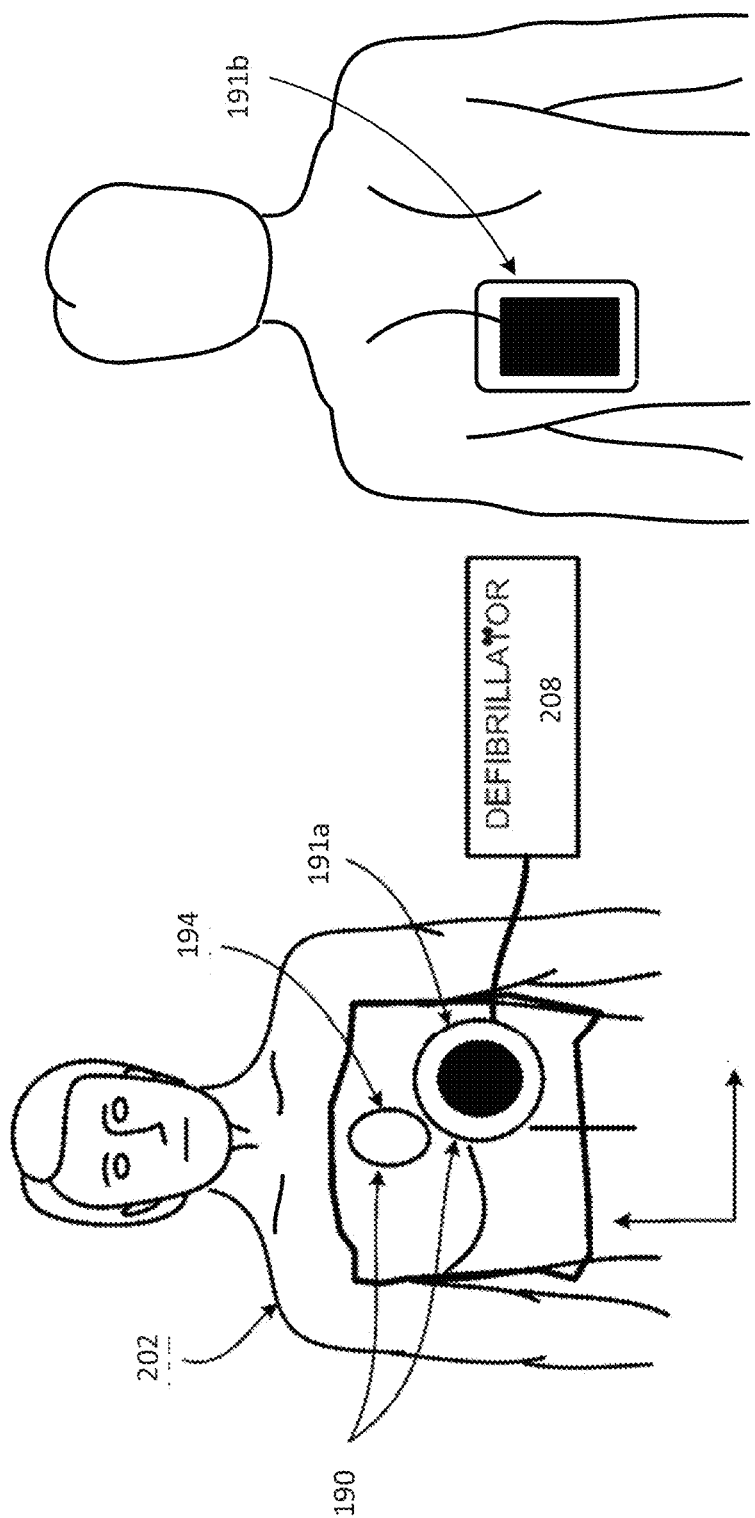

SYSTEM FOR ASSISTING RESCUERS IN PERFORMING CARDIO-PULMONARY RESUSCITATION (CPR) ON A PATIENT

CROSS REFERENCE TO RELATED APPLICATIONS

This application is a continuation of U.S. patent application Ser. No. 16/270,000, which is a continuation of U.S. patent application Ser. No. 15/833,288, which is a continuation-in-part of U.S. patent application Ser. No. 15/601,465, filed May 22, 2017, which is continuation of U.S. patent application Ser. No. 15/178,578, filed Jun. 10, 2016, now U.S. Pat. No. 9,682,009, which is a continuation of U.S. patent application Ser. No. 14/605,653, filed Jan. 26, 2015, now U.S. Pat. No. 9,387,147, which is a continuation of U.S. patent application Ser. No. 14/107,066, filed Dec. 16, 2013, now U.S. Pat. No. 8,979,764, which is a continuation of U.S. patent application Ser. No. 13/555,439 filed on Jul. 23, 2012, now U.S. Pat. No. 8,634,937, which claims priority to U.S. Provisional Application No. 61/527,663 filed Aug. 26, 2011, each of which is incorporated by reference herein in its entirety. U.S. patent application Ser. No. 15/833,288 is also a continuation-in-part of U.S. patent application Ser. No. 15/175,500, filed Jun. 7, 2016, now U.S. Pat. No. 9,839,576, which is a continuation of U.S. patent application Ser. No. 14/299,092 filed Jun. 9, 2014, now U.S. Pat. No. 9,364,680, which is a continuation of U.S. patent application Ser. No. 13/398,280 filed Feb. 16, 2012, now U.S. Pat. No. 8,781,577, which claims benefit of priority to U.S. Provisional Application Ser. No. 61/473,273, filed Apr. 8, 2011, each of which is incorporated by reference herein in its entirety.

BACKGROUND

Field of the Invention

This document relates to cardiac resuscitation, and in particular to systems and techniques for assisting rescuers in performing cardio-pulmonary resuscitation (CPR) and other resuscitative activities.

Description of Related Art

The heart relies on an organized sequence of electrical impulses to beat effectively. Deviations from this normal sequence is known as arrhythmia. Certain medical devices include signal processing software that analyzes electrocardiography (ECG) signals acquired from a medical patient (e.g., a victim at a scene of an emergency) to determine when a cardiac arrhythmia such as ventricular fibrillation (VF) or shockable ventricular tachycardia (VT) exists. These devices include automated external defibrillators (AEDs), ECG rhythm classifiers, and ventricular arrhythmia detectors. An AED is a defibrillator—a device that delivers controlled electrical shock to a patient—while being relatively easy to use, such as by providing verbal prompts to a provider of care to "talk" the provider through a process of evaluating a patient for, attaching the patient to, and activating, AED therapy. Certain of the medical devices just discussed are also capable of recognizing different cardiac waveforms such normal sinus rhythm, aystole, VT and VF.

Many AEDs implement algorithms to recognize the VT and VF waveforms by performing ECG analyses at specific times during a rescue event of a patient using defibrillation and cardio-pulmonary resuscitation (CPR). The first ECG analysis is usually initiated within a few seconds after the defibrillation electrodes are attached to the patient. Typically, if the ECG analysis detects a shockable rhythm, the rescuer is advised to deliver a defibrillation shock.

Following the defibrillator shock delivery or when any of the analyses described above detects a non-shockable rhythm, treatment protocols recommended by the American Heart Association and European Resuscitation Council require performing CPR on the victim for a period of two minutes. The CPR includes rescue breathing and chest compressions. Following this period of CPR, the AED reinitiates ECG analysis as described above. The sequence of one ECG analysis/defibrillation shock followed by 2 minutes of CPR continues in a repetitive fashion for as long as the AED's power is turned on and the patient is connected to the AED device. Typically, the AED provides audio prompts to inform the rescuer when analyses are about to begin, what the analysis results were, and when to start and stop the delivery of CPR.

Many studies have reported that the discontinuation of precordial compression can significantly reduce the recovery rate of spontaneous circulation and 24-hour survival rate for victims. Thus, it is useful to recognize abnormal heart rhythms during chest compressions. There is recent clinical evidence showing that performing chest compressions before defibrillating the patient under some circumstances can be beneficial. Specifically, it is clinically beneficial to treat a patient with chest compressions before defibrillation if the response times of the medical emergency system result in a delay of more than four minutes, such that the patient is in cardiac arrest for more than four minutes. Chest compression artifact rejection can employ spectral analysis of the ECG, defibrillation success prediction, and therapeutic decision-making typically specify a set of parameters in the ECG frequency spectrum to be detected. For example, U.S. Pat. No. 5,683,424 compares a centroid or a median frequency or a peak power frequency from a calculated frequency spectrum of the ECG to thresholds to determine if a defibrillating shock is necessary.

SUMMARY

In some aspects, a method for providing adaptive Cardiopulmonary Resuscitation (CPR) treatment to a person in need of emergency assistance includes obtaining, by a computing unit, from an accelerometer positioned to move in coordination with a patient's breastbone values for depths of a plurality of the chest compressions. The method also includes obtaining, by a computing unit, from a light sensor affixed to the patient information about light detection. The method also includes determining, based on the information from the light sensor, whether a rescuer is releasing the chest of a patient during manual CPR chest compressions. The method also includes providing feedback to a rescuer about chest compressions performed by the rescuer based at least in part on the values for the depths of the plurality of the chest compressions and the determination of whether the rescuer is releasing the chest of the patient.

Embodiments can include one or more of the following.

Determining whether the rescuer is releasing the chest of a patient during manual CPR chest compressions can include determining a frequency at which light is detected by the light sensor, comparing the determined frequency with a compression rate obtained from the accelerometer, and determining that the rescuer is not releasing the chest of a patient if the determined frequency at which light is detected by the light sensor is less than the compression rate obtained from the accelerometer.

Providing the feedback to the rescuer about chest compressions can include displaying on a graphical display screen of a defibrillator, an indication of the depths of one or more of the plurality of the chest compressions, the rate of the chest compressions, and a release indicator.

Providing the feedback to the rescuer about chest compressions can include displaying a release indicator where the amount of fill in the release indicator varies to indicate whether the rescuer is fully releasing between chest compressions.

Providing the feedback to a rescuer about chest compressions can include displaying an icon that indicates whether the chest compressions are being performed properly.

The method can also include receiving information about the patient's heart activity and displaying on a graphical display, with the feedback about chest compressions, an electrocardiogram of the patient.

The computing unit can be integrated with a portable defibrillator.

The computing unit can be a touchscreen tablet computer.

In some aspects, an external defibrillator includes a light sensor arranged to contact a patient and obtain measurements regarding light detection, a computing unit connected to memory that stores computer instructions for determining, based on the information from the light sensor, whether a rescuer is releasing the chest of a patient during manual CPR chest compressions, and a video display screen for displaying feedback to a rescuer about chest compressions performed by the rescuer based at least in part on the determination of whether the rescuer is releasing the chest of the patient.

Embodiments can include one or more of the following.

The computing unit can be configured to determine whether the rescuer is releasing the chest of a patient during manual CPR chest compressions by determining a frequency at which a threshold amount of light is detected by the light sensor, comparing the determined frequency with a compression rate obtained from an accelerometer, and determining that the rescuer is not releasing the chest of a patient if the determined frequency at which a threshold amount of light is detected by the light sensor is less than the compression rate obtained from the accelerometer.

The feedback to the rescuer about chest compressions can include a release indicator.

An amount of fill in the release indicator can vary to indicate whether the rescuer is fully releasing between chest compressions.

The feedback to the rescuer about chest compressions can include an icon that indicates whether the chest compressions are being performed properly.

The external defibrillator can also include one or more sensors configured to obtain information about the patient's heart activity.

The video display can be further configured to display an electrocardiogram of the patient with the feedback about chest compressions.

In some additional aspects, a method for providing adaptive Cardiopulmonary Resuscitation (CPR) treatment to a person in need of emergency assistance includes obtaining, by a computing unit, from an accelerometer positioned to move in coordination with a patient's breastbone values for depths of a plurality of the chest compressions, obtaining, by a computing unit, from a capacitive touch sensor affixed to the patient information about contact with the sensor, determining, based on the information from the capacitive touch sensor, whether a rescuer is releasing the chest of a patient during manual CPR chest compressions, and providing feedback to a rescuer about chest compressions performed by the rescuer based at least in part on the values for the depths of the plurality of the chest compressions and the determination of whether the rescuer is releasing the chest of the patient.

Embodiments can include one or more of the following.

Determining whether the rescuer is releasing the chest of a patient during manual CPR chest compressions can include determining a frequency at which contact with the capacitive touch sensor is detected based on the information from the capacitive touch sensor, comparing the determined frequency with a compression rate obtained from the accelerometer, and determining that the rescuer is not releasing the chest of a patient if the determined frequency at contact is detected by the capacitive touch sensor is less than the compression rate obtained from the accelerometer.

Providing the feedback to the rescuer about chest compressions can include displaying on a graphical display screen of a defibrillator, an indication of the depths of one or more of the plurality of the chest compressions, the rate of the chest compressions, and a release indicator.

Providing the feedback to the rescuer about chest compressions can include displaying a release indicator where the amount of fill in the release indicator varies to indicate whether the rescuer is fully releasing between chest compressions.

Providing the feedback to a rescuer about chest compressions can include displaying an icon that indicates whether the chest compressions are being performed properly.

The method can also include receiving information about the patient's heart activity and displaying on a graphical display, with the feedback about chest compressions, an electrocardiogram of the patient.

In some additional aspects, an external defibrillator includes a capacitive touch sensor arranged to contact a patient and obtain measurements regarding contact with the capacitive touch sensor, a computing unit connected to memory that stores computer instructions for determining, based on the information from the capacitive touch sensor, whether a rescuer is releasing the chest of a patient during manual CPR chest compressions, and a video display screen for displaying feedback to a rescuer about chest compressions performed by the rescuer based at least in part on the determination of whether the rescuer is releasing the chest of the patient.

Embodiments can include one or more of the following.

The computing unit can be configured to determine whether the rescuer is releasing the chest of a patient during manual CPR chest compressions by determining a frequency at which a capacitance indicative of contact of a rescuer's hands with the capacitive touch sensor is detected by the capacitive touch sensor, comparing the determined frequency with a compression rate obtained from an accelerometer, and determining that the rescuer is not releasing the chest of a patient if the determined frequency at which a threshold amount of light is detected by the light sensor is less than the compression rate obtained from the accelerometer.

The feedback to the rescuer about chest compressions can include a release indicator with an amount of fill in the release indicator varying to indicate whether the rescuer is fully releasing between chest compressions.

The feedback to the rescuer about chest compressions can include an icon that indicates whether the chest compressions are being performed properly.

The defibrillator can be further configured to receive information about the patient's heart activity and displaying on a graphical display, with the feedback about chest compressions, an electrocardiogram of the patient.

In some additional aspects, a system for assisting a rescuer in performing cardio-pulmonary resuscitation (CPR) on a patient is provided. The system comprises: a proximity sensor configured to be positioned at a location corresponding to a location of a rescuer's hand when delivering compressions to a patient's chest, the proximity sensor configured to produce a signal indicative of the rescuer's hands being released from the patient's chest; a medical device operatively coupled with the proximity sensor and configured to provide resuscitative treatment to the patient; and a controller communicatively coupled with the medical device and the proximity sensor. The controller is configured to: determine, based upon the signal from the proximity sensor, if the rescuer's hands have been released from the patient's chest, and trigger an action by the medical device in response to a determination that the rescuer's hands have been released from the patient's chest.

The proximity sensor can comprise at least one of a capacitive sensor, an ultrasonic sensor, an E-field sensor, and a light emitter-receiver pair. The determination that the rescuer's hands have been released from the patient's chest can be based on a measurement from the proximity sensor that the rescuer's hands are greater than 1 cm away from the patient's chest.

The medical device can be a defibrillator comprising an electrical storage device capable of delivering a therapeutic pulse to a patient. The action can be charging the electrical storage device of the defibrillator.

At least one sensor can be operatively connected to the controller for obtaining one or more electrocardiogram (ECG) signals from the patient. The controller can be further configured to: determine, based upon the signal from the proximity sensor, if the rescuer's hands are in contact with the patient's chest, analyze the one or more ECG signals from the patient during delivery of chest compressions to the patient, and determine a desirability of a shock to the patient based on the analysis of the one or more ECG signals during the delivery of chest compressions of a CPR cycle. The action can be an analysis of one or more ECG signals acquired in an absence of chest compressions to reconfirm the desirability of the shock to the patient, the absence of chest compressions being based on the determination of whether the rescuer's hands have been released from the patient's chest. In some examples, the controller can be configured to: perform at least one transformation of at least a portion of the one or more ECG signals from the patient into frequency domain data based on the determination of whether the rescuer's hands have been released from the patient's chest, determine a first frequency-based value over a first evaluation period based on the at least one transformation, determine a second frequency-based value representing a trend over a second evaluation period based on the at least one transformation, determine a probability of therapeutic success based at least in part on the first frequency-based value and the second frequency-based value, and provide an indication of the probability of therapeutic success. The first frequency-based value can comprise an amplitude spectral area (AMSA) value and the second frequency-based value comprises an AMSA trend.

The medical device can comprise a feedback device operatively connected to the controller. The feedback device can be configured to provide feedback received from the controller to the rescuer regarding compressions. The action can be providing an indication via the feedback device to provide ventilation to the patient. The indication can be at least one of an audio indication and a visual indication.

In some additional aspects, a method for assisting a rescuer in performing cardio-pulmonary resuscitation (CPR) on a patient comprises: positioning a proximity sensor at a location corresponding to a location of a rescuer's hand when delivering compressions to a patient's chest; producing, with the proximity sensor, a signal indicative of the rescuer's hands being released from the patient's chest; determining, based upon the signal from the proximity sensor, if the rescuer's hands have been released from the patient's chest; and triggering an action by a medical device in response to a determination that the rescuer's hands have been released from the patient's chest.

The method may also comprise obtaining one or more electrocardiogram (ECG) signals from the patient. The method may also further comprise: determining, based upon the signal from the proximity sensor, if the rescuer's hands are in contact with the patient's chest, analyzing the one or more ECG signals from the patient during delivery of chest compressions to the patient; and determining a desirability of a shock to the patient based on the analysis of the one or more ECG signals during the delivery of chest compressions of a CPR cycle. The action can be an analysis of one or more ECG signals acquired in an absence of chest compressions to reconfirm the desirability of the shock to the patient, the absence of chest compressions being based on the determination of whether the rescuer's hands have been released from the patient's chest.

Alternatively, the action can be: performing at least one transformation of at least a portion of the one or more ECG signals from the patient into frequency domain data based on the determination of whether the rescuer's hands have been released from the patient's chest; determining a first frequency-based value over a first evaluation period based on the at least one transformation; determining a second frequency-based value representing a trend over a second evaluation period based on the at least one transformation; determining a probability of therapeutic success based at least in part on the first frequency-based value and the second frequency-based value; and providing an indication of the probability of therapeutic success. The first frequency-based value may comprise an amplitude spectral area (AMSA) value and the second frequency-based value comprises an AMSA trend.

The action can also be providing an indication to ventilate the patient.

Other features and advantages will be apparent from the description and drawings, and from the claims.

BRIEF DESCRIPTION OF THE DRAWING(S)

FIGS. 9A and 9B are diagrams of a victim receiving CPR.

FIGS. 10A and 10B are diagrams showing the placement of the hands relative to a capacitive sensor during the administration of CPR to a victim.

FIGS. 11A and 11B show anterior and posterior electrode assemblies, respectively, applied to a patient.

DESCRIPTION OF THE INVENTION

This description discusses systems and techniques for using a proximity sensor to assist in resuscitation efforts of a patient. A proximity sensor may be used to detect whether the hands of a rescuer or a compression device is in contact with a patient. Depending on whether there is contact, various actions that are helpful to enhance resuscitation of the patient may be triggered.

In certain embodiments, the proximity sensor may generate information for providing feedback to a user/rescuer about the quality of CPR chest compressions. For example, detection of whether the hands are in contact with the patient may useful to determine whether the rescuer is appropriately releasing the chest of the victim during chest compressions, or whether the rescuer has initiated contact with the patient to begin a chest compression.

When it is determined that the rescuer has paused chest compressions for a brief interval of time (e.g., 1-3 seconds, 1-5 seconds, 1-10 seconds), then other activities may be performed. For example, during the pause, it may be beneficial to perform certain types of analyses on the ECG of the patient (e.g., ECG shock analysis, frequency transform analysis, amplitude spectrum area analysis). That is, artifacts that arise in the ECG due to the administration of chest compressions may be avoided by confirming or otherwise detecting that a chest compression is not occurring and performing the calculation or analysis during the pause in chest compression. Also, during pauses in chest compressions, it may be preferable to administer one or more positive pressure breath ventilations to the patient. Such a pause in chest compressions may be sufficiently long for a ventilation to be safely administered to the patient. Otherwise, the pressure generated within the thorax due to a chest compression may be injurious to the patient if a positive pressure ventilation is administered concurrently with chest compressions.

Figures 1A, 1B:
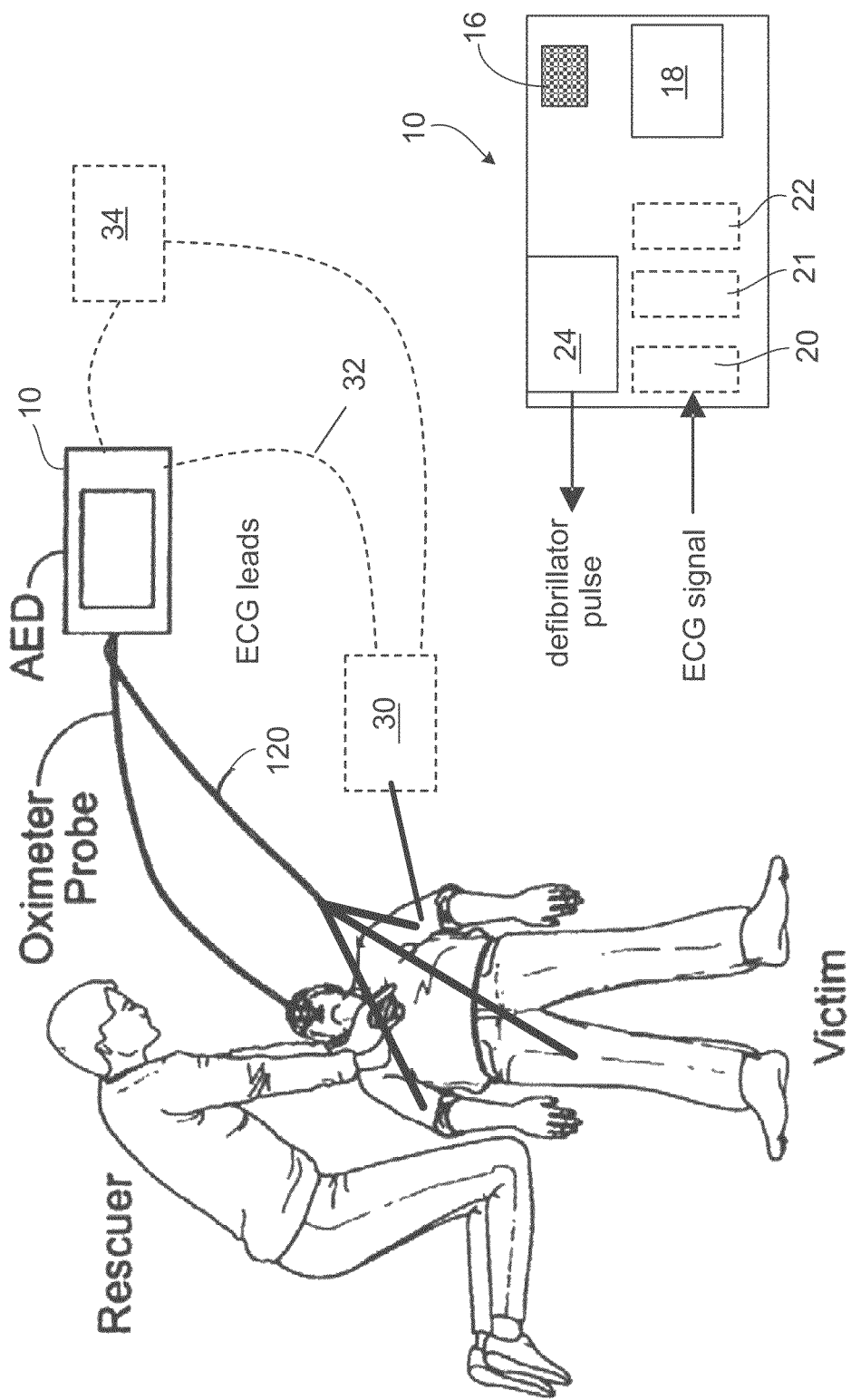
FIG. 1A is a diagram of one implementation including an automatic electronic defibrillator (AED) and a multiple lead electrocardiograph (ECG) device.
FIG. 1B is a diagram of the AED of FIG. 1A.

Referring now to FIG. 1A, an AED 10 is shown that may be used to provide a defibrillation shock at an appropriate time. In the figure, which shows an example implementation, a rescuer uses an AED 10 to automatically monitor a victim during cardiac resuscitation. The AED 10 uses measured ECG signals to monitor the victim's heart, and charges the defibrillation device within the AED while the victim is resuscitated using chest compressions techniques. In some examples, the manner in which the defibrillation device is charged (e.g., the rate of charge, the total amount of charge stored) can be based on the measured ECG signals. Advantageously, charging the defibrillation device during CPR chest compressions reduces the amount of time that the victim is not receiving chest compressions because, if a shockable rhythm exists, the device is armed and ready to deliver the shock as soon as the rescuer completes the chest compressions.

As shown in FIG. 1B, the AED 10 includes a speaker 16, a display screen 18, an analog-to-digital converter 20, a processor 22, and a defibrillator pulse generator 24. The analog-to-digital converter 20 is connected to a set of ECG leads that are in turn attached to the victim. The ECG leads pass signals to the processor 22 for monitoring the electrical rhythms of the victim's heart. The converter 20 sends the signals from the ECG leads to the processor 22. The processor 22 monitors the victim's heart for dangerous rhythms using the ECG signals while the victim is resuscitated using chest compressions techniques.

If the AED 10 detects a dangerous heart rhythm, the AED 10 generates an alert signal. The alert signal is noticeable to the rescuer. The AED 10 can generate a defibrillating shock to the victim when the rescuer issues a command to the AED 10 directing such a shock. The defibrillating shock is intended to remedy the dangerous rhythm of the victim's heart.

The AED 10 also includes a charging module that may be configured to charge the AED during chest compressions. The module can adaptively charge the AED based on monitored ECG signals and patient age. In some examples, the defibrillator is pre-charged only if a shockable rhythm is likely to exist as determined by analysis of the monitored ECG signals. In some additional examples, the level of charge for the device is determined and set based on the monitored ECG signals. In some additional examples, the method of charging (e.g., the rate of charge) varies based on the monitored ECG signals in an effort to conserve power. For example, if time allows, a capacitor may be charged more slowly than it normally would in order to conserve power, but still ensure that the capacitor will reach its full charge just as the defibrillator is needed by the rescuer.

The AED 10 uses a rhythm advisory method for, a) quantifying the frequency-domain features of the ECG signals; b) differentiating normal and abnormal ECG rhythms, such as VF; c) detecting the onset of abnormal ECG rhythms; and d) making decisions about the physiological states of the heart. This frequency-domain measure can be reliable with or without the presence of the chest compression artifact in the ECG signals. The AED 10, after identifying the current physiological state of the heart, can make a decision about appropriate therapeutic action for the rescuer to make and communicate the action to the rescuer using the speaker 16 and the display screen 18.

The AED 10 may incorporate functionality for performing additional therapeutic actions such as chest compressions, ventilations, or delivery of intravenous solution-containing metabolic or constitutive nutrients. Based on the results of the analysis of the rhythm advisory method, the AED 10 may automatically deliver the appropriate therapy to the patient.

The AED 10 may also be configured in "advisory" mode wherein the AED 10 will prompt the caregiver after the AED 10 has made a determination of the best therapy, and acknowledgement by the caregiver/device operator, in the form of a button press or voice-detected acknowledgement, is required before therapy is delivered to the patient.

The AED 10 analyzes the ECG signals to predict defibrillation success as well as to decide whether it is appropriate to defibrillate or to deliver an alternative therapy such as chest compressions, drugs such as epinephrine, constitutive nutrients such as glucose, or other electrical therapy such as pacing.

In some examples, one or more therapeutic delivery devices 30 automatically deliver the appropriate therapy to the patient. The therapeutic delivery devices 30 can be, for example, a portable chest compression device, a drug infusion device, a ventilator and/or a device that includes multiple therapies such as defibrillation, chest compression, ventilation and drug infusion. The therapeutic delivery devices 30 are physically separate from the defibrillator AED 10, and control of the therapeutic delivery devices 30 may be accomplished by a communications link 32. The communications link 32 may take the form of a cable but preferably the link 32 is via a wireless protocol.

In other examples, control and coordination for the overall resuscitation event and the delivery of the various therapies may be accomplished by a device 34 or processing element that is external to the AED 10. For instance, the device 34 may download and process the ECG data from the AED 10; analyze the ECG signals, perform relevant determinations like those discussed above and below based on the analysis, and control the other therapeutic devices 30, including the AED 10. In other examples, the AED 10 may perform all the processing of the ECG, including analyzing the ECG signals, and may transmit to the control device 34 only the final determination of the appropriate therapy, whereupon the control device 34 would perform the control actions on the other linked devices 30.

Chest compression artifacts can be separated from the ECG signal components, making it possible for the AED 10 to process the ECG signal without halting the processing during chest compressions. Exemplary methods for analyzing the ECG signal to determine if a shockable rhythm exists are described, for example, in U.S. Pat. No. 7,565,194, titled "ECG Rhythm Advisory Method," the contents of which are hereby incorporated by reference in their entirety.

It has been recognized that good chest compressions during CPR is essential to saving more victims of cardiac arrest. The compression rate recommended by the American Heart Association in its guidelines is equal or greater than 100 compressions per minute. Many studies have reported that the discontinuation of chest compressions, such as is commonly done for ECG analysis and charging of a defibrillator, can significantly reduce the recovery rate of spontaneous circulation and 24-hour survival rate. Because of safety issues with delivery of a high voltage defibrillation shocks with voltages of 1000-2000 volts, rescuers are taught to cease chest compressions and remove their hands from the victim's chest before initiating the defibrillation shock. By analyzing ECG signals during chest compressions as a mechanism to permit earlier charging of an energy delivery device (e.g., a capacitor) in a defibrillator device, the gaps in providing chest compressions can be reduced, and patient care increased.

Figure 2:
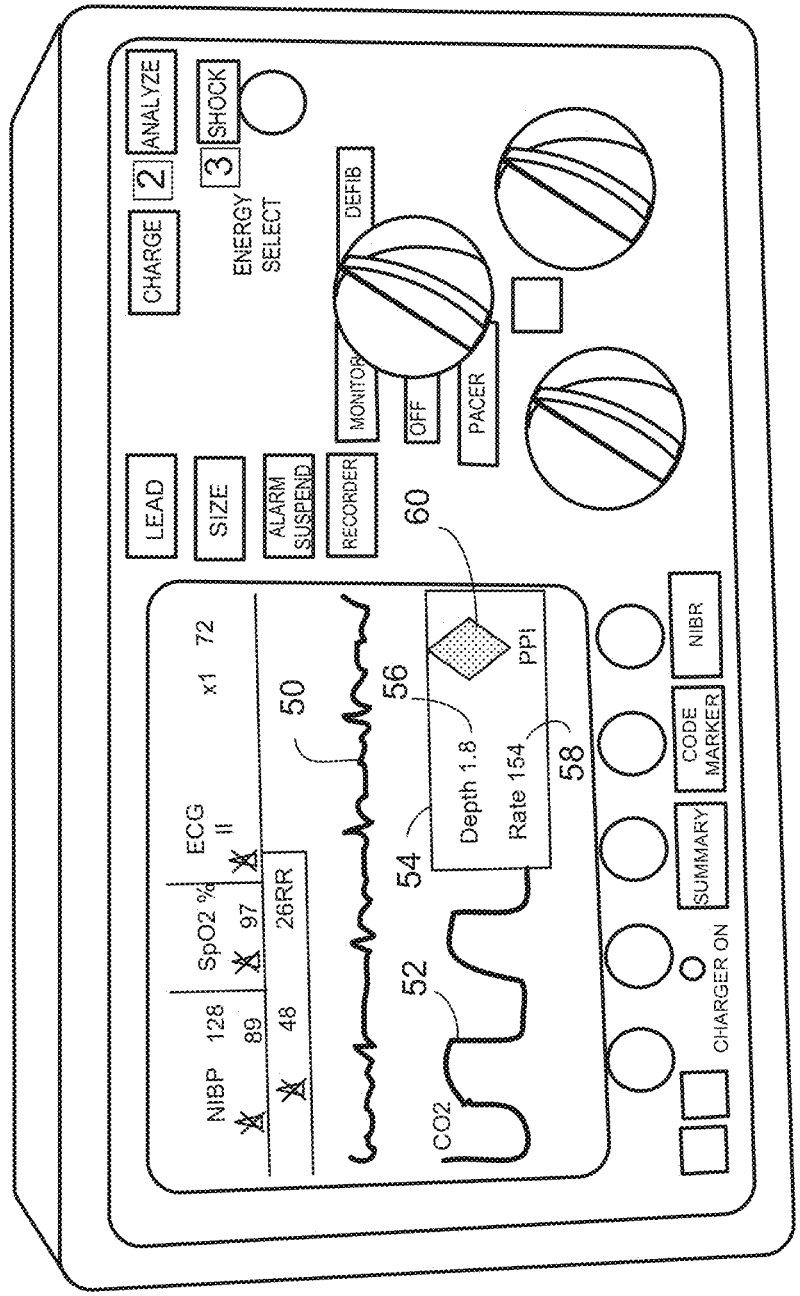
FIG. 2 is a diagram of a defibrillation device with a display.

FIG. 2 shows a defibrillation device with a display portion that provides information about patient status and CPR administration quality during the use of the defibrillator device. The data is collected and displayed in an efficient and effective manner to a rescuer. As shown on the display, during the administration of chest compressions, the device displays information about the chest compressions in box 54 on the same display as a filtered ECG waveform 50 and a $CO_2$ waveform 52 (alternatively a $SpO_2$ waveform can be displayed).

During chest compressions, the ECG waveform is generated by gathering ECG data point and accelerometer readings and filtering the motion induced (e.g., CPR induced) noise from the ECG waveform. Measurement of velocity or acceleration of chest compression during chest compressions can be performed according to the techniques taught by U.S. Pat. No. 7,220,335, Method and Apparatus for Enhancement of Chest Compressions During Chest Compressions, the contents of which are hereby incorporated by reference in their entirety. Displaying the filtered ECG waveform helps clinicians reduce interruptions in CPR because the displayed waveform is easier for the rescuer to decipher. If the ECG waveform is not filtered, artifacts from manual chest compressions make it difficult to discern the presence of an organized heart rhythm unless compressions are halted. Filtering out this artifact allows clinicians to view the underlying rhythm without stopping chest compressions.

As shown in the display, the filtered ECG waveform 50 is a full length waveform filling the entire span of the display device while the second waveform (e.g., the $CO_2$ waveform 52) is a partial length waveform and fills only a portion of the display. A portion of the display beside the second waveform provides the CPR information in box 54. For example, the display splits the horizontal area for the second waveform in half, displaying waveform 52 on left and CPR information on the right in box 54.

The CPR information in box 54 is automatically displayed when compressions are detected. The information about the chest compressions displayed in box 54 includes rate 58 (e.g., number of compressions per minute) and depth 56 (e.g., depth of compressions in inches or millimeters). The rate and depth of compressions can be determined by analyzing accelerometer readings. Displaying the actual rate and depth data (in addition to or instead of an indication of whether the values are within or outside of an acceptable range) is believed to provide useful feedback to the rescuer. For example, if an acceptable range for chest compression depth is between 1.5-2 inches, providing the rescuer with an indication that his/her compressions are only 0.5 inches can allow the rescuer to determine how to correctly modify his/her administration of the chest compressions.

The information about the chest compressions displayed in box 54 also includes a perfusion performance indicator (PPI) 60. The PPI 60 is a shape (e.g., a diamond) with the amount of fill in the shape differing to provide feedback about both the rate and depth of the compressions. When CPR is being performed adequately, for example, at a rate of about 100 compressions/minute (CPM), with the depth of each compression greater than 1.5 inches, the entire indicator will be filled. As the rate and/or depth decreases below acceptable limits, the amount of fill lessens. The PPI 60 provides a visual indication of the quality of the CPR such that the rescuer can aim to keep the PPI 60 completely filled. While some exemplary types of information displayed to the rescuer have been described herein, additional information about CPR quality and physiological parameters of the victim can be displayed in conjunction with or instead of the information described herein. For example, a release indication can be displayed with other information about the CPR quality of measured physiological parameters. Exemplary displays and measurements are described, for example, in Ser. No. 13/025,348 filed on Feb. 11, 2011, now U.S. Pat. No. 8,880,166, issued on Nov. 4, 2014 and entitled "DEFIBRILLATOR DISPLAY" and in Ser. No. 13/081,217 filed on Apr. 6, 2011, now U.S. Pat. No. 9,364,625, issued on Jun. 14, 2016 and entitled "WIRELESS VENTILATOR REPORTING," the contents of each of which are hereby incorporated by reference.

In addition to measuring information about the rate and depth of CPR chest compressions, in some examples the defibrillator device provides information about whether the rescuer is fully releasing his/her hands at the end of a chest compression. For example, as a rescuer tires, the rescuer may begin leaning on the victim between chest compressions such that the chest cavity is not able to fully expand at the end of a compression. If the rescuer does not fully release between chest compressions the quality of the CPR can diminish. As such, providing a visual or audio indication to the user when the user does not fully release can be beneficial.

Figure 3:
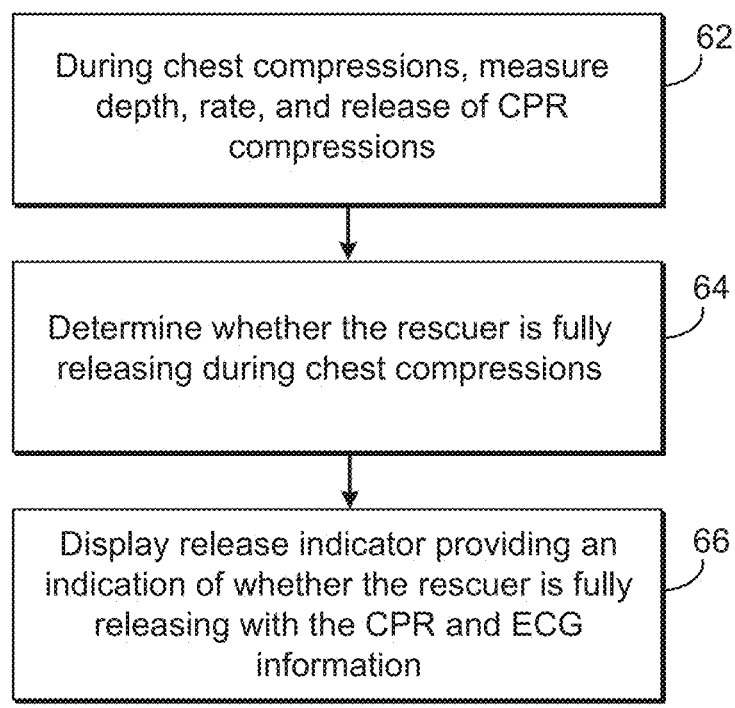
FIG. 3 is a flow chart showing actions taken to provide a release indicator.
Figure 4A:
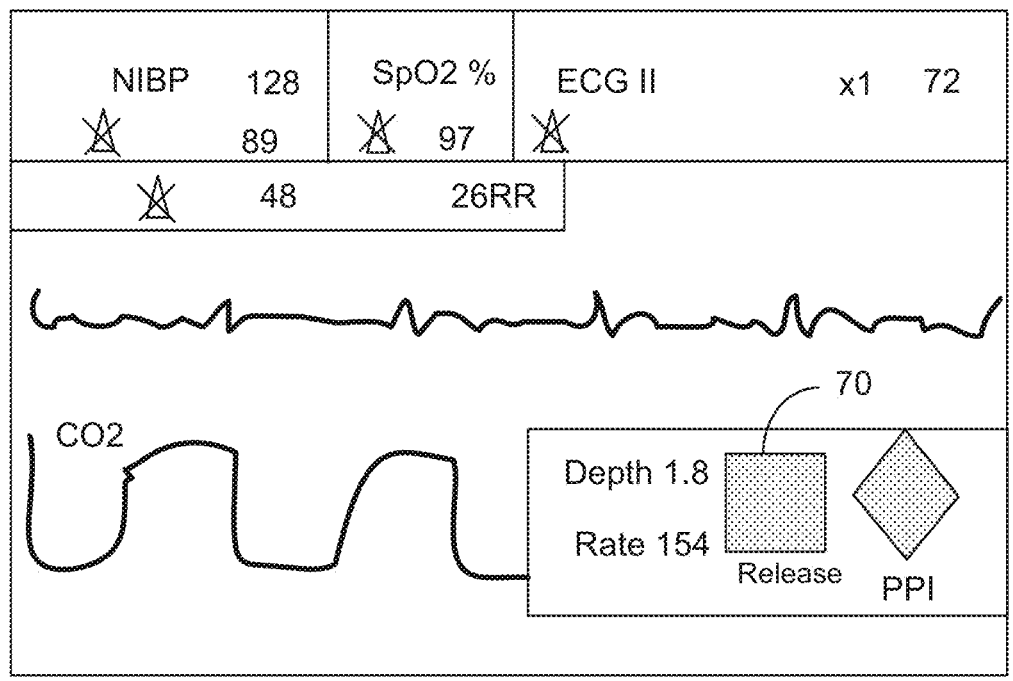
FIGS. 4A and 4B are screenshots showing exemplary information presented on a defibrillator display.
Figure 4B:
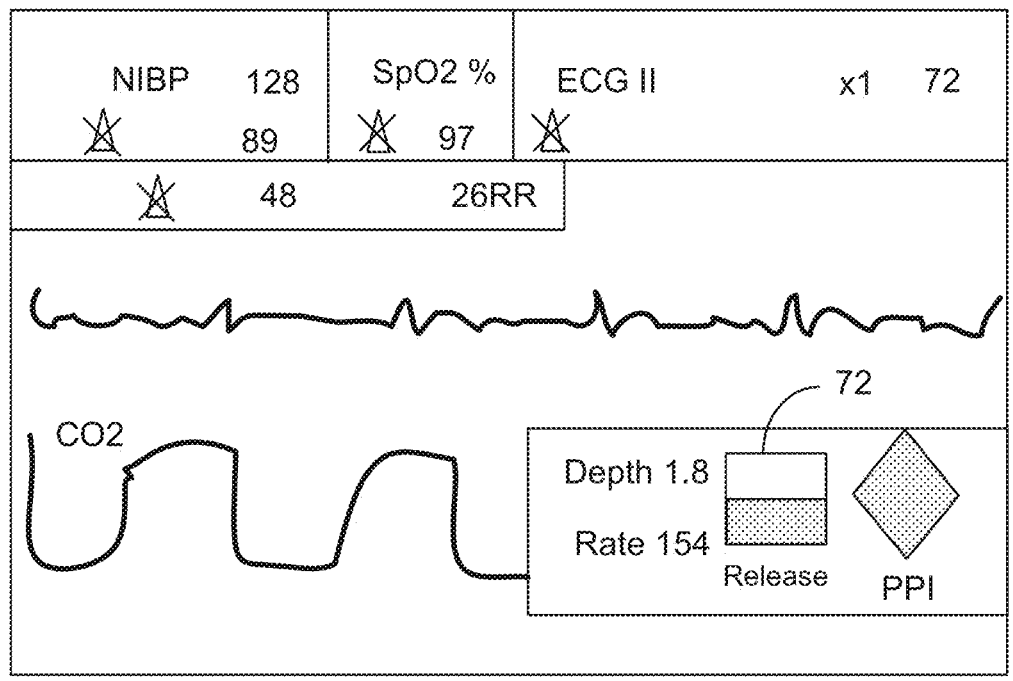

FIG. 3 is a flow chart showing actions taken to provide an indication of whether a rescuer is fully releasing between chest compressions. At box 62, the defibrillator device measures depth, rate, and release of CPR chest compressions. The depth, rate, and release of CPR chest compressions can be determined based on information collected from an accelerometer, light sensor, capacitive touch sensor, or other devices. Based on the collected information, at box 64, the defibrillator determines whether the rescuer is fully releasing between chest compressions. At box 66, the defibrillator provides an indicator on a display that includes information about whether the rescuer is fully releasing. For example, the display on the defibrillator can include a release indication box where the amount of fill in the box varies to indicate whether the rescuer is fully releasing between chest compressions. For example, as shown in FIG. 4A, when the rescuer is fully releasing the box 70 can be fully filled. When the rescuer is not fully releasing the amount of fill in the release indication box is decreased such that the box is only partially filled (e.g., as shown in box 72 of FIG. 4B).

Figure 5:
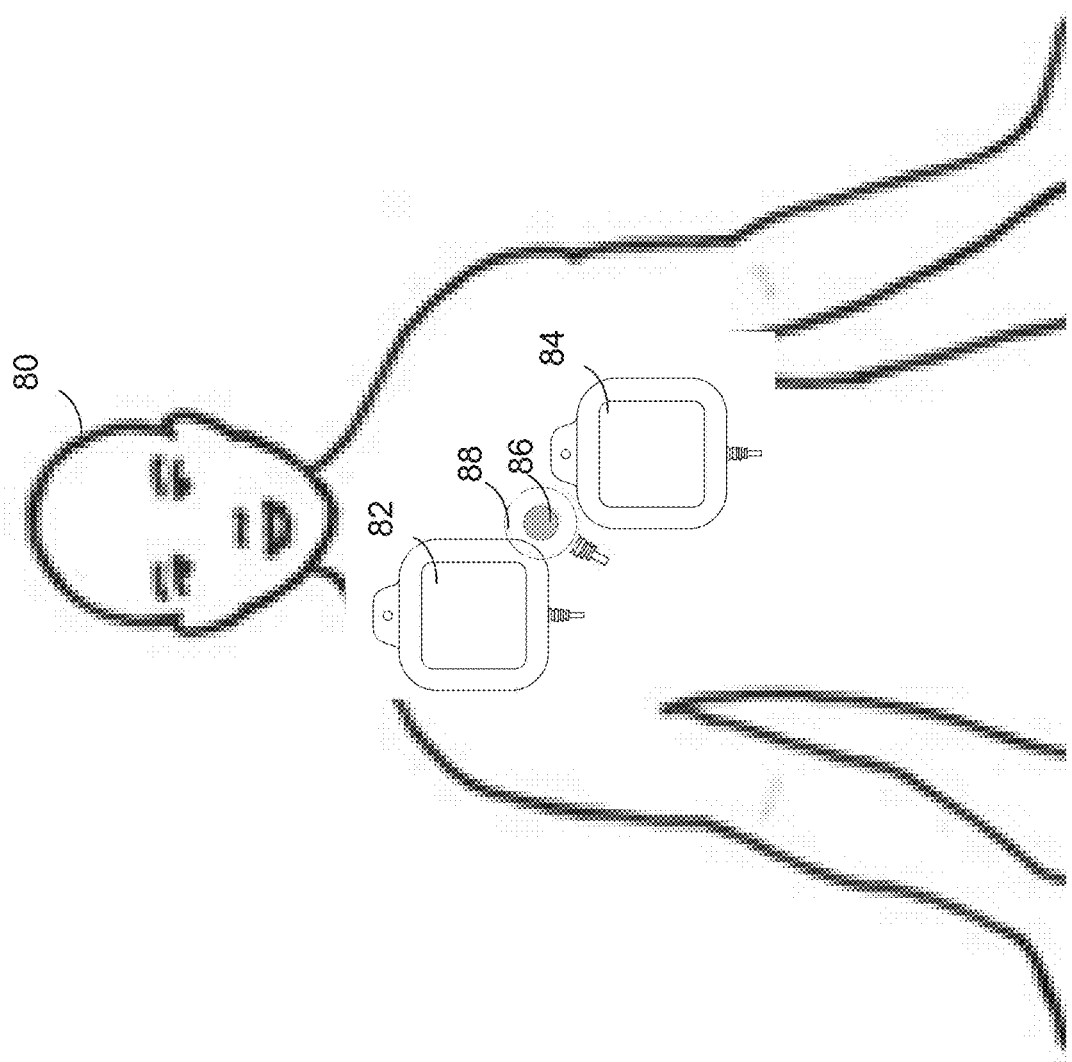
FIG. 5 is a diagram of defibrillation electrodes attached to a victim.

In some examples, the depth and rate of CPR chest compressions can be determined based on information collected from an accelerometer while the release of the CPR chest compressions can be based on information collected from a light or capacitive touch sensor, or some other type of proximity sensor. For example, as shown in FIG. 5, a CPR monitoring device 86 that includes a light sensor or capacitive touch sensor 88 and an accelerometer can be affixed to a victim's chest at a location corresponding to the location of the rescuer's hands when delivering manual chest compressions prior to the administration of CPR. The light sensor measures light impinging on the sensor and provides the information to a computing device in the defibrillator. The defibrillator processes the information to determine whether the rescuer's hands are in contact with the light sensor 88. More particularly, because the device 86 is affixed to the victim's chest or on top of the CPR sensor at a location corresponding to the location of the rescuer's hands when delivering manual chest compressions, the presence or absence of light detection by the light sensor 88 can be used to determine whether the rescuer is making contact with the patient's body. That is, based on information detected from the sensor(s) (e.g., proximity sensor, accelerometer, E-field sensor, light sensor, etc.), it can be determined whether the rescuer is initiating a chest compression or whether the rescuer is fully releasing the chest of the victim during the administration of chest compressions.

Practically speaking, depending on the type of proximity sensor employed, the proximity sensor measures a signal indicative of a relevant physical property (e.g., E-field, capacitance, light reflected from the rescuer's hands, ambient light, etc.) and then the relative proximity of the hands to the patient is estimated. For example, for a light sensor, if a substantial amount of light is sensed, then the hands may be estimated to be relatively far away from the patient; conversely if a small amount or no light is sensed, then the hands may be estimated to be close to, or perhaps in contact with, the patient. An appropriate threshold or suitable criterion may be employed to determine whether the values produced by the proximity sensor would qualify as the hands being in contact with the patient or not in contact with the patient.

The light sensor 88 can be any device that is used to detect light. Exemplary light sensors include photocells or photoresistors that change resistance when light shines on it, charged coupled devices (CCD) that transport electrically charged signals, photomultipliers that detect light and multiply it, and the like. Capacitive sensing is a technology based on capacitive coupling between conductive or has a dielectric different than that of air and the sensor. When the human hands approaches or touches the capacitive sensor, this detects this movement or touch of the hand and measure a change in capacitance. The level of capacitance can be used by the processor or device to determine whether the rescuer hand is touching the capacitor sensor pad. For example, the processor or device may analyze the level of capacitance recorded by the capacitive sensor and determine whether the level of capacitance falls within a set criterion for whether the hands are in contact with the patient or not in contact with the patient.

As discussed herein, any suitable proximity sensor may be employed. The output of the proximity sensor is calibrated according to methods known by those of skill in the art to estimate a distance of the rescuer's hands from the patient. For instance, a greater amount of light sensed by a light sensor may indicate that the rescuer's hands are further away from the patient. Similarly, the recorded capacitance, voltage, E-field, or other value, may be indicative of the distance of the rescuer's hands from the patient. In various embodiments, if the estimated distance of the rescuer's hands from the patient is greater than a certain distance (e.g., greater than 1 mm, greater than 5 mm, greater than 1 cm, greater than 2 cm, greater than 3 cm, greater than 4 cm, greater than 5 cm, greater than 6 cm, greater than 7 cm, greater than 8 cm, greater than 9 cm, greater 10 cm, etc.), then it may be determined that the rescuer's hands are not in contact with the patient, or released from (following a compression) the patient.

Figure 6A:
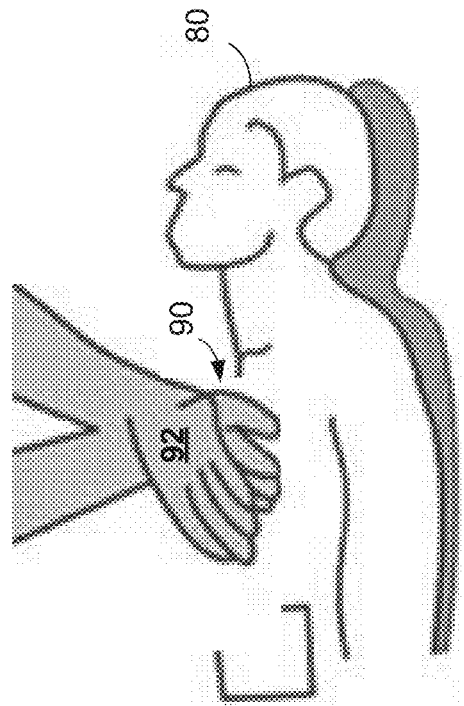
FIGS. 6A and 6B are diagrams of a victim receiving CPR.
Figure 6B:
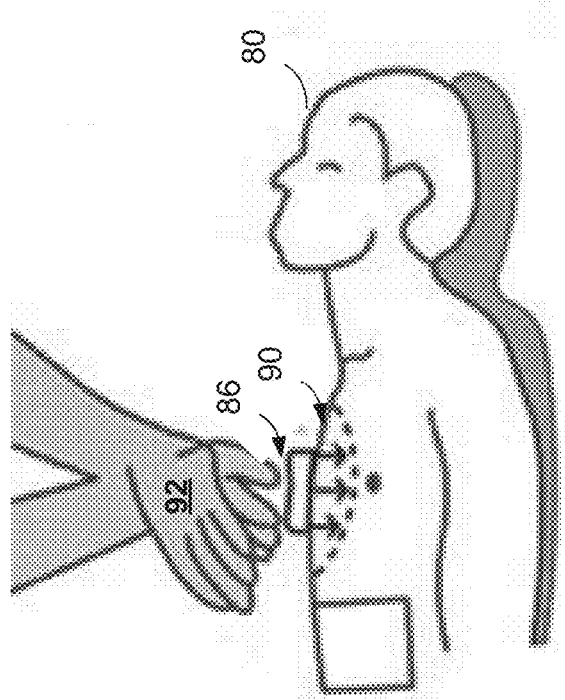
Figure 7A:
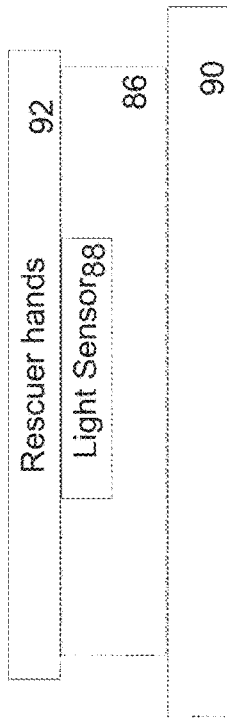
FIGS. 7A and 7B are diagrams showing the placement of the hands relative to a light sensor during the administration of CPR to a victim.
Figure 7B:
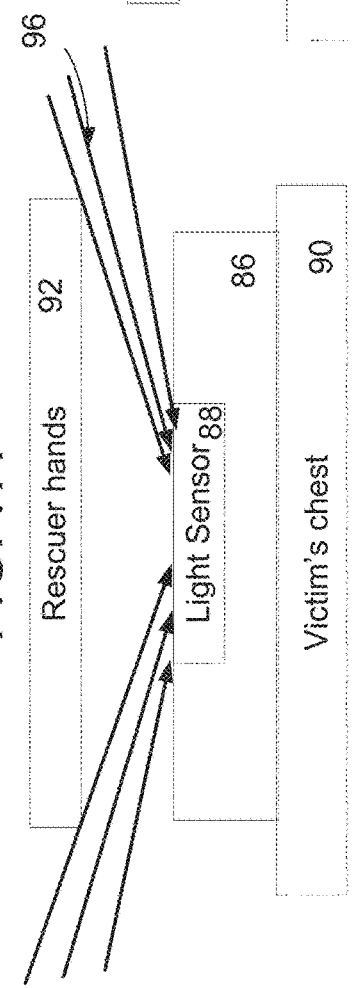

FIGS. 6A-B and 7A-B show exemplary light sensor during CPR compressions. As shown in FIGS. 6A and 7A, when the rescuer's hands 92 are raised away from the victim's chest and are not in contact with the victim's chest 90 (e.g., when the rescuer releases from a compression), the light sensor 88 is uncovered. Thus, when the rescuer's hands are raised away from the victim's chest light 96 can reach the light sensor 88 and the light sensor detects the presence of the light 96. In contrast, as shown in FIGS. 6B and 7B, when the rescuer's hands 92 are in contact with the victim's chest 90 (e.g., when the rescuer is providing a compression) the light sensor 88 is covered. When the light sensor is covered, light is not able to reach the light sensor 88. Thus, the presence and absence of light measured by the light sensor can be used to determine whether the rescuer is fully releasing his/her hands from the victim's chest 90; when light is detected the rescuer has released and when light is not detected the rescuer is maintaining physical contact with the victim. Similarly, when the rescuer's hands are off the chest, it can then be determined whether the rescuer has made contact with the patient so as to initiate a subsequent chest compression. When the rescuer has initiated contact, information from the accelerometer can then be used to determine the chest compression depth.

In some examples, the information from the light sensor can be compared to CPR compression rate information from the accelerometer to determine whether the user is releasing the victim's chest fully. More particularly, if the rescuer is releasing the victim's chest fully, light should be observed by the light sensor for every compression. Thus, the defibrillation device can determine a frequency at which a threshold amount of light is detected by the light sensor and compare the determined frequency with a compression rate obtained from the accelerometer. If the determined frequency from the light sensor is the same (or within an acceptable range from) the compression rate obtained from the accelerometer, the defibrillation device can determine that the rescuer is appropriately releasing the victim's chest. On the other hand, if the frequency from the light sensor is less than the compression rate, the defibrillation device can determine that the rescuer is not appropriately releasing the victim's chest.

While in the example described above, the presence/absence of light was used to determine the release of the rescuer's hands from the victim's chest, in some additional examples a change in light measured by the light sensor 88 can be used to determine the presence/absence of the rescuer's hands. For example, the rescuer may not fully cover the light sensor 88 when providing compressions. However, if a portion of the light sensor 88 is covered, a change in the intensity or amount of light measured by the light sensor will be observed when the rescuer lifts his/her hands. This change in intensity can be used to determine presence/absence of the rescuer's hands.

In some additional examples, the light sensor 88 can be used to detect the removal of the electrodes from a package and can be used to begin instructions to a rescuer about how to apply the electrodes to the victim.

Figure 8A:
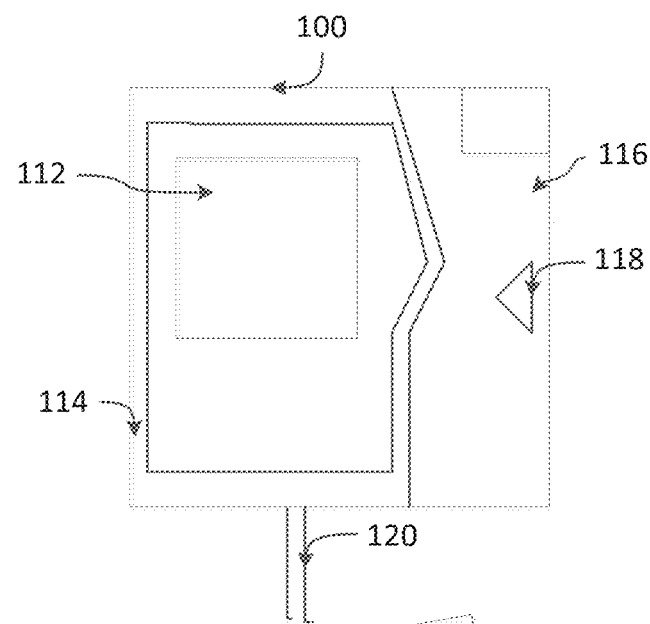
FIG. 8A shows an electrode package.

FIG. 8A shows an assembled electrode package 100 with multiconductor electrical lead 120 and label 112. The package is opened by grasping the loose flaps 116 at arrow label 118, and peeling back the top flap. As the flaps are pulled apart, releaseable peripheral adhesive 114 parts. When a light sensor is included in the assembled electrode package 110, light is unable to impinge on the light sensor 161. As such, information from the sensor can be used to determine that the rescuer has not yet opened the electrode package regardless of whether the leads 120 have been plugged into a defibrillation device. As such, if the defibrillation device detects that the leads 120 have been inserted into the defibrillation device but the light sensor 161 does not indicate the presence of light, the defibrillation device can provide instructions to the rescuer about how to open the electrode package 100.

Figure 8B:
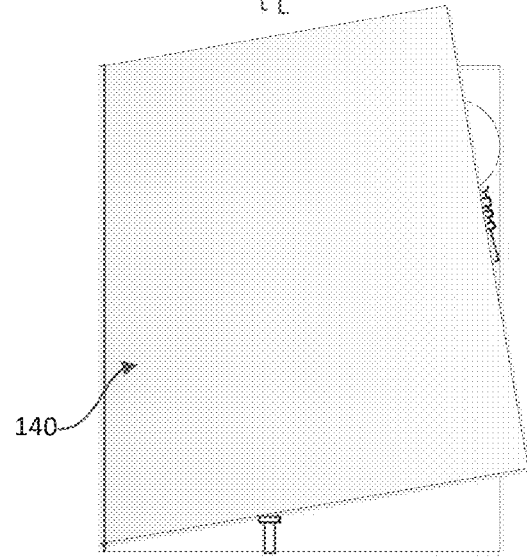
FIGS. 8B and 8C show defibrillation electrodes prior to removal from a backing.
Figure 8C:
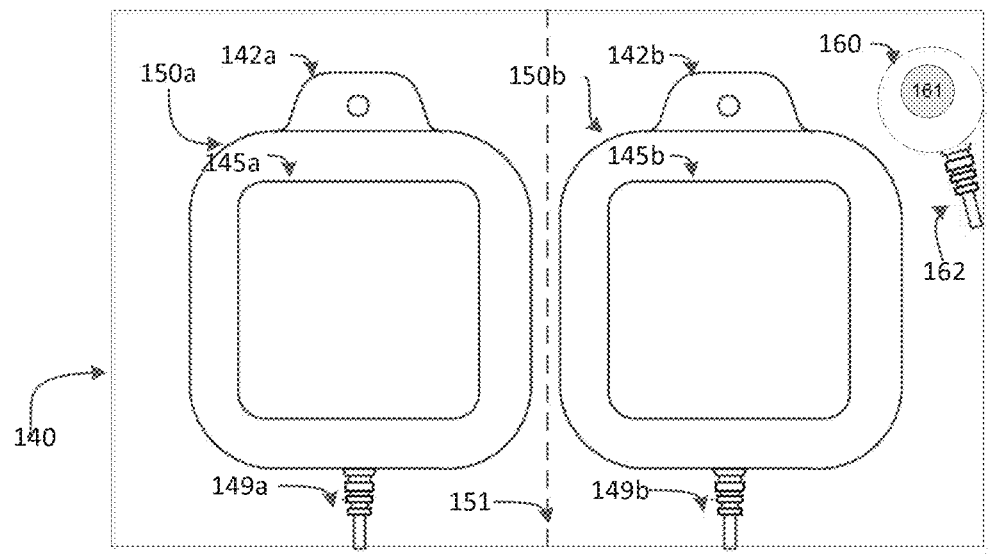

FIGS. 8B and 8C show views of the electrodes 150a and 150b, an accelerometer 160, a light sensor 161, and styrene sheet 140 after removal from the electrode package 100. Before the package is opened, the styrene sheet 140 is folded along fold line 151 in the form of a closed book (e.g., as shown in FIG. 8B), with the electrodes 150a and 150b and accelerometer 160 peelably attached to the interior facing surfaces of the book. The accelerometer works with electronics in the defibrillator to determine the depth of compressions during CPR. The light sensor 161 works with electronics in the defibrillator to determine whether the rescuer is appropriately releasing the victim's chest between compressions (e.g., as described herein). ECG electrodes (not shown) are built into one of electrode 150a or 150b (each is located at approximately the corners of the triangular shape of the electrode). Until the book is unfolded, the light sensor 161 is covered by the opposite side of the styrene sheet 140 and light is unable to impinge on the light sensor. On opening the package, the book is unfolded, so that the electrodes and accelerometer are presented to the user as shown in FIG. 8C. Upon unfolding the book, the light sensor 161 is uncovered and light is able to reach the light sensor. Thus, the unfolding of the book (and the resulting light measurement from the sensor 161) indicates to the defibrillation device that the user has opened the package 100 and is ready to receive information (e.g., audio or visual instructions) about the application of the electrodes to the victim.

FIGS. 9A-B and 10A-B show a capacitive sensor during CPR compressions. As shown in FIGS. 9A and 10A, when the rescuer's hands 92 are raised away from the victim's chest and are not in contact with the victim's chest 90 (e.g., when the rescuer releases from a compression), the capacitive sensor 87 is uncovered. Thus, when the rescuer's hands are raised away from the victim's chest capacitive measured by the capacitive sensor 87 is based on the dielectric of air. In contrast, as shown in FIGS. 9B and 10B, when the rescuer's hands 92 are in contact with the victim's chest 90 (e.g., when the rescuer is providing a compression) the capacitive sensor 87 is covered and contact is made between the rescuer's hands and the sensor 87. When the human hands approach or touch the capacitive sensor 87, the sensor 87 detects this movement or touch of the hand and measures a change in capacitance. Thus, the measured capacitance level can be used by the processor or device to determine whether the rescuer hand is touching the capacitor sensor 87 and can be used to determine whether the rescuer is fully releasing his/her hands from the victim's chest 90; when capacitance remains at a level indicating that the rescuer's hands are in contact with the capacitive sensor 87, the rescuer is not fully releasing his/her hands between compressions.

In some examples, the information from the capacitive sensor can be compared to CPR compression rate information from the accelerometer to determine whether the user is releasing the victim's chest fully. More particularly, if the rescuer is releasing the victim's chest fully, a change in capacitive should be observed by the capacitive sensor for every compression. Thus, the defibrillation device or other device used for resuscitation can determine a frequency at which a threshold change in capacitance is detected by the capacitive sensor and compare the determined frequency with a compression rate obtained from the accelerometer. If the determined frequency from the capacitive sensor is the same (or within an acceptable range from) the compression rate obtained from the accelerometer, the defibrillation device can determine that the rescuer is appropriately releasing the victim's chest. On the other hand, if the frequency from the capacitive sensor is less than the compression rate, the defibrillation device can determine that the rescuer is not appropriately releasing the victim's chest.

While at least some of the embodiments described above describe techniques and displays used in conjunction with an AED device, similar techniques and displays can be used with other defibrillator or resuscitative devices. Exemplary professional grade defibrillator devices include the R series, E series, Propaq MD, or M series devices manufactured by ZOLL Medical, MA and the Philips MRX or Philips XL devices.

Additionally, the defibrillator may take the form of a wearable defibrillator such as the LifeVest, manufactured by ZOLL Medical (Chelmsford, MA).

Further to the discussion above, good quality compressions with little or no pausing (e.g., substantially continuous administration of compressions) are important for cardiac arrest survival. However, it is difficult for the average rescuer to provide continuous, high quality manual compressions without pauses. In one example, the systems and methods described herein are configured to automatically detect the cessation or pausing of a rescuer's manual administration of chest compressions and supplement the treatment of the patient with electrical stimulation during the time periods of such pauses. The electrical stimulation begins automatically based on detected characteristics related to the manual administration of chest compressions such that the time period between cessation or pausing of the manual chest compressions and administration of the electrical stimulation is brief (e.g., less than 10 seconds, less than 5 seconds, less than 3 seconds). Examples of such electrical stimulation are described in detail in U.S. patent application Ser. No. 15/175,500, published as US2016/0296418, which is hereby incorporated by reference in its entirety.

In some examples, the electrical stimulation can be administered by, for example, an anterior electrode assembly (AEA) 190 affixed to the victim's 202 thorax as described in relation to FIGS. 11A and 11B below. FIGS. 11A and 11B show anterior and posterior electrode assemblies, respectively, applied to a patient.

The AEA 190 is composed of a defibrillation/pacing/monitoring electrode 191 known to those skilled in the art, composed of a conductive adhesive gel in contact with the patient's skin, typically also a conductive metallic surface on the conductive gel for distributing the current delivered by the stimulation device, such as a defibrillator 208, and an insulative top layer. Thus, the AEA 190 can be removably affixed to the patient's thorax. A housing 194 containing a motion sensor along with power and signal conditioning electronics is positioned on the patient's sternum, and is used to measure the motion of the sternum during CPR chest compressions. The motion sensor may be an accelerometer as is used commercially in devices of this type (ZOLL CPR Stat-Padz, Chelmsford, Mass.) or may be a pressure sensor, a velocity sensor such as those employing a time-varying magnetic flux and coil arrangement or other varied motion sensors. Defibrillator 208 processes conditioned motion sensor signal via a Sternal Motion analysis subsystem 226 to determine when the rescuer has ceased chest compressions, paused in the administration of chest compressions, or is no longer administering effective chest compressions. The Sternal Motion analysis subsystem 226 can be, for example, a software function that is part of the software code for running the Defibrillator 208 in general, or may be specialized hardware either in the defibrillator or in the housing 194 that may communicate to the defibrillator microprocessor 230 via, for instance, a serial communication channel such as USB, RS232 or Bluetooth. During the course of any typical CPR interval, the duration of which is typically on the order of 2 minutes, a rescuer may stop briefly at multiple points, sometimes for as little as 3-10 seconds.

Figure 12:
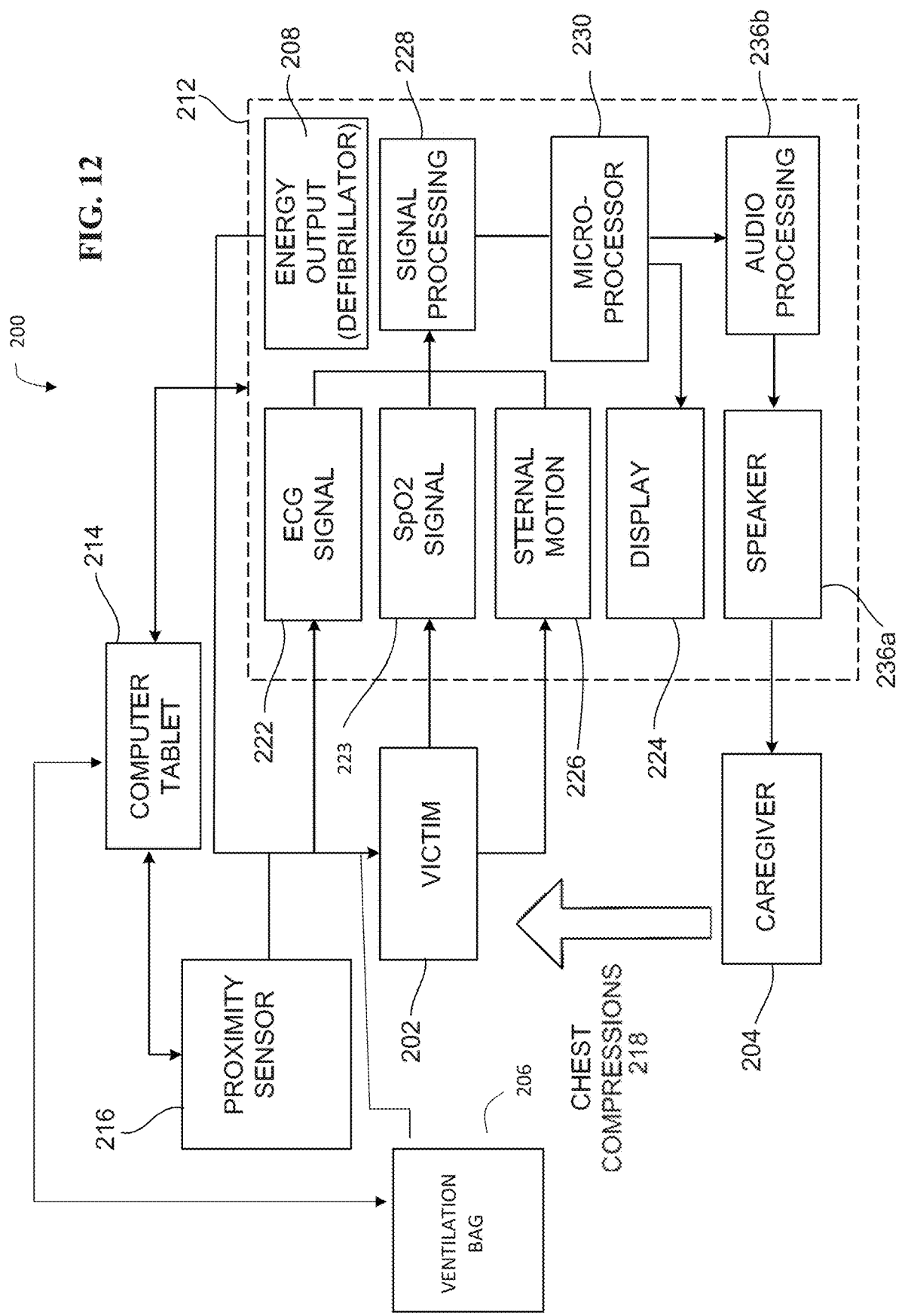
FIG. 12 is a block diagram of an exemplary system.
Figure 13:
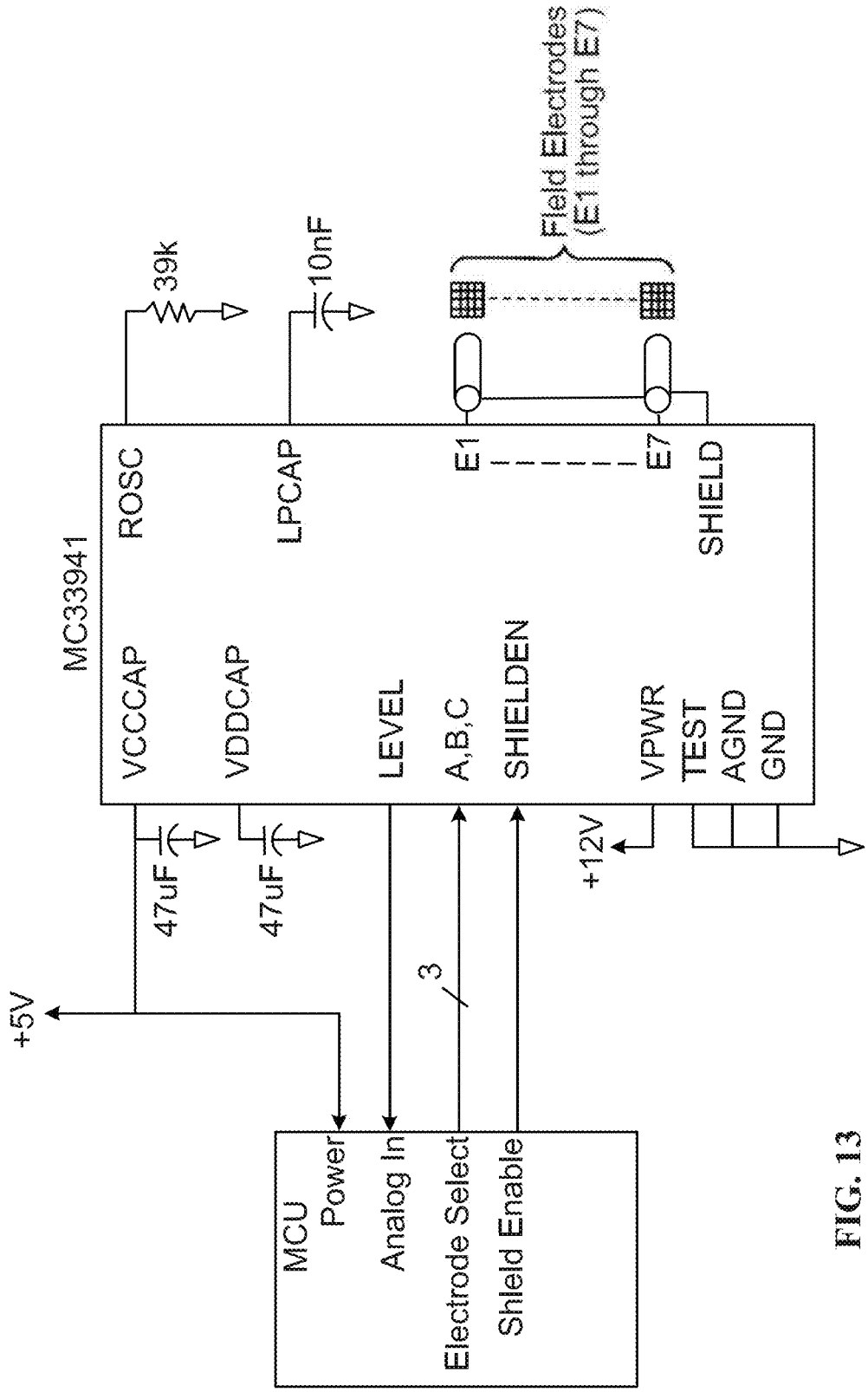
FIG. 13 shows a schematic for an E-field proximity sensor.

FIG. 12 shows an example system 200 for assisting a rescuer in performing resuscitation activities, in schematic form, and for providing dynamically controlled chest compression to a patient. In general, the system 200 involves a number of medical devices that may be used to provide life-saving care to a victim, such as a victim 202, of sudden cardiac arrest. The various devices may be part of a single unit or multiple units, and may be used to monitor various real-time physical parameters of the victim 202, to communicate between the components and with remote systems such as central caregivers, and to provide care to the victim 202 or provide instructions to caregivers, such as caregiver 204, in providing care to the victim 202.

The victim 202 in this example is an individual who has apparently undergone sudden cardiac arrest is being treated by the caregiver 204. The caregiver 204 may be, for example, a civilian responder who has had limited training in lifesaving techniques, an emergency medical technician (EMT), a physician, or another medical professional. The caregiver 204 in this example may be acting alone or may be acting with assistance from one or more other caregivers, such as a partner EMT.

The victim 202 is in a position in which therapy has been provided to the victim 202. For example, a set of defibrillator electrodes have been applied to the victim's torso in a typical manner and are in wired connection to a portable external defibrillator 208. The defibrillator 208 may be, for example, a typical automated external defibrillator (AED), a professional defibrillator, or other similar type of defibrillating apparatus. The victim 202 has also been provided with a ventilation bag 206, to provide forced air into the victim's longs to assist in rescue breathing of the victim 202. The defibrillator 208 and ventilation bag 206 may be operated in familiar manners and in coordination by various caregivers. Also, the ventilation bag 206 may be fitted with various sensors and transmitters so as to communicate electronically with the defibrillator 208. For example, a volumetric flow sensor may be provided with the ventilation bag 206, and data about the volume of airflow to and from the victim may be passed to defibrillator 208, so the defibrillator 208 may relay such information, or may also use such information to affect the manner in which defibrillation is provided to the victim 202.

A computer tablet 214 is also shown communicating with the other devices, and being manipulated by caregiver 204. The tablet may serve as a general electronic command post for the caregiver 204 to receive information about the victim 202 and other items, to communicate with other caregivers, and to provide input in controlling the operation of the various components in the system 200. The tablet 214 may be provided with short range and long range wireless communication capabilities, such as Bluetooth or WiFi on the one hand, and cellular 3G or 4G on the other. The caregiver 204 may input information into the tablet computer 214, such as information describing the condition of the victim 202 and other similar information that is to be recognized and recorded by the caregiver 204. The tablet 214 may also be in data communication with multiple sensors for sensing real-time information about the victim 202, such as blood pressure, pulse, and similar real-time patient parameters. The caregiver 204 may also input information into tablet 214 so as to control one or more of the medical devices being used with the victim 202. For example, the user may adjust the type, intensity, speed, or coordination of treatment that is provided to the victim 202.

Chest compression are delivered manually by the Caregiver 204. In such a case, audiovisual feedback is provided to the Caregiver 204 via Speaker 236a, operatively coupled to audio processing circuitry 236b, and display 224. Feedback will direct the caregiver 204 to deliver compressions less forcefully when necessary.

As shown in this example, multiple different input signals are received that characterize the current real-time condition or physical parameters of the victim 202. For example, an ECG signal 222 may be received by the MPU 212 and may represent current and real time ECG waveforms for the victim 202, which may be obtained by leads connected to defibrillator 208.

An SpO2 signal 223, or other physiologically-derived signal that is either a direct or indirect measure of circulatory flow or perfusion, is also captured at display 224, and may be used to further determine when and at what force to apply chest compressions to the victim 202.

Note that while FIG. 12 shows specific examples of input signals such as SpO2, an apparatus could use any combination of physiological signals such as, but not limited to: ECG; measures of cardiac output; measures of heart rate; blood pressure(s); oxygen saturation (SpO2); heart sounds (including phonocardiography); heart imaging (including ultrasound); impedance cardiography. Compression parameters could use any combination of features or measurements of compression including, but not limited to: compression velocity; compression depth; duty cycle; velocity of downstroke and upstroke; intrathoracic pressures during compressions; pleural pressures during compressions; sternal position, velocity or acceleration; chest wall or sternal strain or deformation; force applied to the chest; pressure used to compress the chest by a mechanical chest compressor.

A signal processing unit 228 is provided to filter inputs, such as ECG inputs, received from the patient for further analysis by the Microprocessor 230. For example, the signal processing unit 228 may filter noise from input signals, and in the case of ECG data may filter artifacts created by chest compression motion of the victim 202 in order to remove such artifacts. Such preparation of ECG signals may be termed SEE-THRU CPR, and can be performed as discussed in U.S. Pat. No. 6,865,413, filed Jan. 23, 2002, and entitled ECG SIGNAL PROCESSOR AND METHOD, the teachings of which are incorporated herein by reference in their entirety.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

The computer system may include software for implementing an electronic patient care record, for example the ePCR software of ZOLL Data Systems (Broomfield Colo.). The software provides the ability to enter, store and transmit patient information as well as therapeutic interactions. The computer is often a so-called "Tablet" computer system that has been ruggedized for pre-hospital use, but may also take the form of an iPhone or iPad. Data is preferably transmitted in real time between the portable "Tablet" computer 214 to the MPU 212.

In some embodiments, the sensor housing 194 and electrodes are configured to ensure that the rescuer's hands have been removed from the patient (e.g., are not in contact with the patient) prior to administration of a defibrillation shock and or delivery the electrical stimulations for generating perfusion. For example, the sensor housing can include a proximity sensor (e.g., a capacitive sensor) that determines whether a rescuer is in contact with the patient and prohibits delivery of electrical current to the patient when the rescuer is in contact with the patient. In some additional examples, as described in more detail below, the system can be configured to coordinate the delivery of the defibrillation shock with the detection that the rescuer has removed his/her hands from the patient. For example, the defibrillation shock can be delivered automatically and without requiring further user action upon detection that the rescuer has removed his/her hands from the patient.

The sensor housing 194 may also contain the proximity sensor 216 for measuring the location of the rescuer's hands. This measurement of rescuer hand location may be used in several possible ways. In cases where the electrode assembly AEA 190 does not incorporate an insulative sheet, the hand location measurement may be used to hold off EPS (e.g., prohibit delivery of electrical pulses) until the rescuer has removed their hands from the patient's chest. Additionally, upon detection of fatigue or cessation of manual chest compressions, the device can provide audio and/or visual prompting to the rescuer instructing them to remove their hands from patient's chest, or to properly release the hands from the patient's chest, until such time as they do remove their hands. The hand measurement may also be used as a triggering mechanism for delivery of therapeutic electromagnetic energy (e.g., defibrillation shock) to the patient. It is believed that automatically delivering the therapeutic electromagnetic energy upon detection of the removal of the rescuer's hands can reduce the time between cessation of manual chest compressions and delivery of the therapeutic electromagnetic energy. For example, the defibrillator may be charged during delivery of the manual chest compressions such that the therapeutic electromagnetic energy can be delivered immediately (e.g., within less than 1 second) after the cessation of manual chest compressions.

Without the automatic detection of the removal of the rescuer's hands and using the detection to trigger the delivery of the therapeutic electromagnetic energy, when treating a patient who has a shockable rhythm, the defibrillator may be charged by a second rescuer while the first delivers ongoing compressions. At the moment for delivering a shock, however, the first rescuer controlling the defibrillator will have the rescuer delivering stop compressions until after the shock is delivered by the first rescuer. This involves a set of clearance commands between the two rescuers, such as saying, "Stand Clear. You're clear. I'm clear. We're all clear", then pressing the shock button when the first rescuer has made sure that no one is touching the patient. This process can cause for period of no delivery of therapeutic compressions for 5-10 seconds (e.g., the time lapse between cessation of chest compressions until the delivery of the electromagnetic energy can be 5-10 seconds). With the automatic detection of the rescuer proximity to the patient, the first rescuer arms the defibrillator, and then the second rescuer who has their hands on the sensor housing 194, delivering the compressions, actually causes the defibrillator to deliver the defibrillation shock by simply lifting their hands from off the sensor. Thus, the electromagnetic energy is automatically delivered upon detection of the removal of the rescuer's hands from the patient. This is believed to be particularly effective because the only person who will be in contact with the patient is the compressor at that point, and they are in the best position to assess whether anyone else might be in contact. When the rescuer lifts their hands off the sensor housing 194, the proximity sensor 216 detects that the rescuers hands have been removed from proximity of the patient and then automatically delivers the shock.

In some embodiments, E-field sensing such as that provided by the MC33941 (Freescale Semiconductor, document Number: MC33941, Rev 4) can be used (e.g., as shown in FIG. 10). Because this method of proximity sensing is fundamentally a measure of stray capacitance embodied by the rescuer's hands, it is important to calibrate to each rescuer because of the variable capacitance interjected by the use of medical gloves, etc. Calibration is accomplished automatically during the time that compressions are occurring. Because the sensor housing is being depressed during compressions, it can be safely assumed, particularly at the time when compression is at its deepest point, that the rescuer hands are in direct contact with the surface of the sensor housing 194. The measured capacitance at that point is taken as the zero-distance reference point.

There are additional benefits beyond minimizing the compression pauses during defibrillation. For instance, it is believed that synchronizing the defibrillation shock to the early phase of the compression upstroke significantly improves shock efficacy. By shocking immediately after detection of loss of rescuer hand contact, the defibrillation shock can be timed to the optimal phase of the compression cycle.

In some additional embodiments, rather than delivering the defibrillation shock immediately upon detection of removal of the rescuer's hands from the patient, one to ten EPS pulses may also be delivered immediately prior to the defibrillation shock, after the proximity sensor 216 and processor have detected loss of contact with the rescuer's hands. The defibrillation shock is then synchronized to the optimal phase of the final EPS pulse.

Alternatives to the E-field proximity sensor 216 are ultrasonic sensors such as the MINI_A PB Ultrasonic transducer (SensComp, MI) that has a measurement range of 1-12 inches. Alternatively, a light emitter-receiver pair may be located on the rescuer-facing upper surface of the sensor housing 194 and be used to detect the instant there is a physical separation between surface of the sensor housing 194 and the rescuer's hands.

Figure 14:
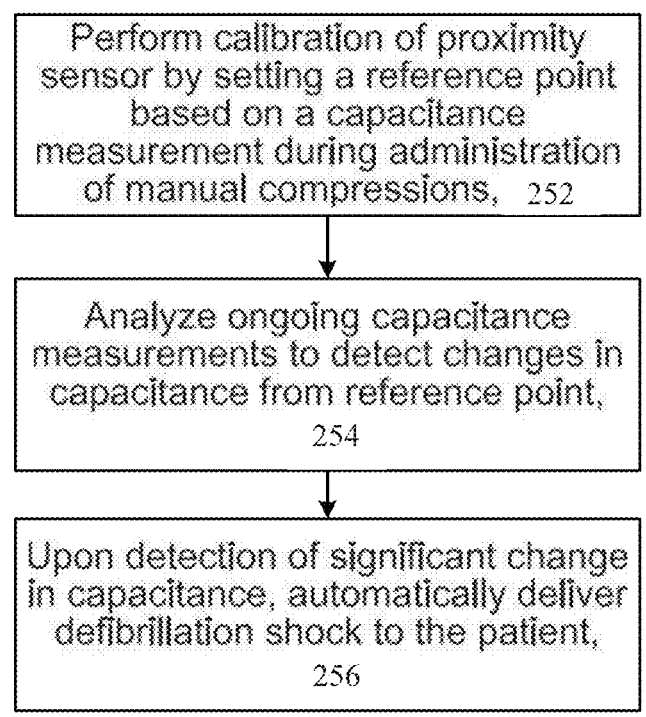
FIG. 14 is a flow chart of a method for detecting and using a rescuer's proximity to determine when to deliver a defibrillation shock.

FIG. 14 is a flow chart of a method for automatically delivering a defibrillation shock based on the detection of the removal of a rescuer's hands from a patient. The system performs a calibration of a proximity sensor by setting a reference point based on a capacitance measurement when compressions are being administered 252. The system analyzes ongoing capacitance measurements to detect changes in capacitance from reference point 254. Upon detection of significant change in capacitance (e.g., a change indicative of removal of the rescuer's hands from the patient), the system automatically delivers a defibrillation shock to the patient 256.

In many examples it is beneficial to detect when a rescuer has released his/her hands from a patient's chest following chest compressions and/or detect when a rescuer's hands make contact with a patient's chest to initiate chest compressions for a variety of reasons. This information can be determined using the proximity sensors discussed hereinabove. Once the system determines that the rescuer has released his/her hands from the patient's chest following chest compressions and/or detects when the rescuer's hands make contact with a patient's chest to initiate chest compressions, the system can also use this information to take various actions as discussed hereinafter.

A. Reconfirmation of the Desirability of Delivering a Shock

In certain instances, AED devices utilize a brief period of time (e.g., while the rescuer locates and presses the button) after the rescuer ceases chest compressions to reconfirm the desirability of delivering the shock to the victim. For example, a rescuer can be instructed to visually inspect and confirm that a shockable rhythm exists and/or the AED device can continue to collect and analyze ECG signals (in the absence of chest compressions resulting in less artifacts in the ECG signal) to re-confirm the desirability of delivering the shock. In general, a time period for re-confirmation based on analysis of an ECG signal without chest compression artifacts can be brief (e.g., less than about 5 seconds, less than about 3 seconds, less than about 2 seconds). The time period for re-confirmation can be based on physiological characteristics (e.g., heart rate that is fast or slow) and/or a desired confidence level for the ECG analysis. Such reconfirmation is discussed in United States Patent Application Publication No. 2016/0220833, which is hereby incorporated by reference in its entirety. Through the use of a proximity sensor, such as proximity sensor 216, the defibrillator may automatically initiate this reconfirmation of whether the patient's ECG is of a shockable or non-shockable nature once the proximity detector detects that the rescuer's hands have been removed from the patient's chest. Examples of reconfirmation and the use of the proximity detector are discussed in greater detail below.

In some examples, the caregiver may halt the CPR treatment (e.g., due to express instruction to halt CPR treatment, during the natural course of repetitive CPR treatment, and/or during ventilations) while some of the data after completion of CPR treatment is being collected and analyzed for further confirmation of an initial determination of whether the rhythm is shockable or not shockable. As discussed herein, confirmation of an initial determination of shockability is sometimes referred to as a reconfirmation mode which may allow for filtered, eliminated or otherwise reduced CPR artifact in the signal during analysis, but it may pose a potential danger to the patient depending on how long the CPR treatment is halted. Thus, if the evaluation of clauses against time segments of the data is successful in determining the state of the patient after a relatively short amount of time, e.g., less than 6 seconds, the CPR treatment can resume relatively quickly, reducing risk to the patient. By detecting the exact moment at which the rescuer ceases chest compressions utilizing the proximity sensor, the time period in which CPR treatment is halted for the reconfirmation mode is minimized.

In some implementations, some or all of the ECG data being acquired is stored during a reconfirmation mode of a CPR treatment, when ECG analysis occurs during CPR treatment and during a brief period after CPR treatment. In reconfirmation mode, the CPR treatment may be temporarily halted so that the CPR treatment does not affect the signal being acquired for confirming the recommendation of whether to administer a defibrillating shock. In some examples, the reconfirmation mode is terminated, and the caregiver is prompted to reconvene CPR treatment, when sufficient ECG data has been acquired.

Figure 15:
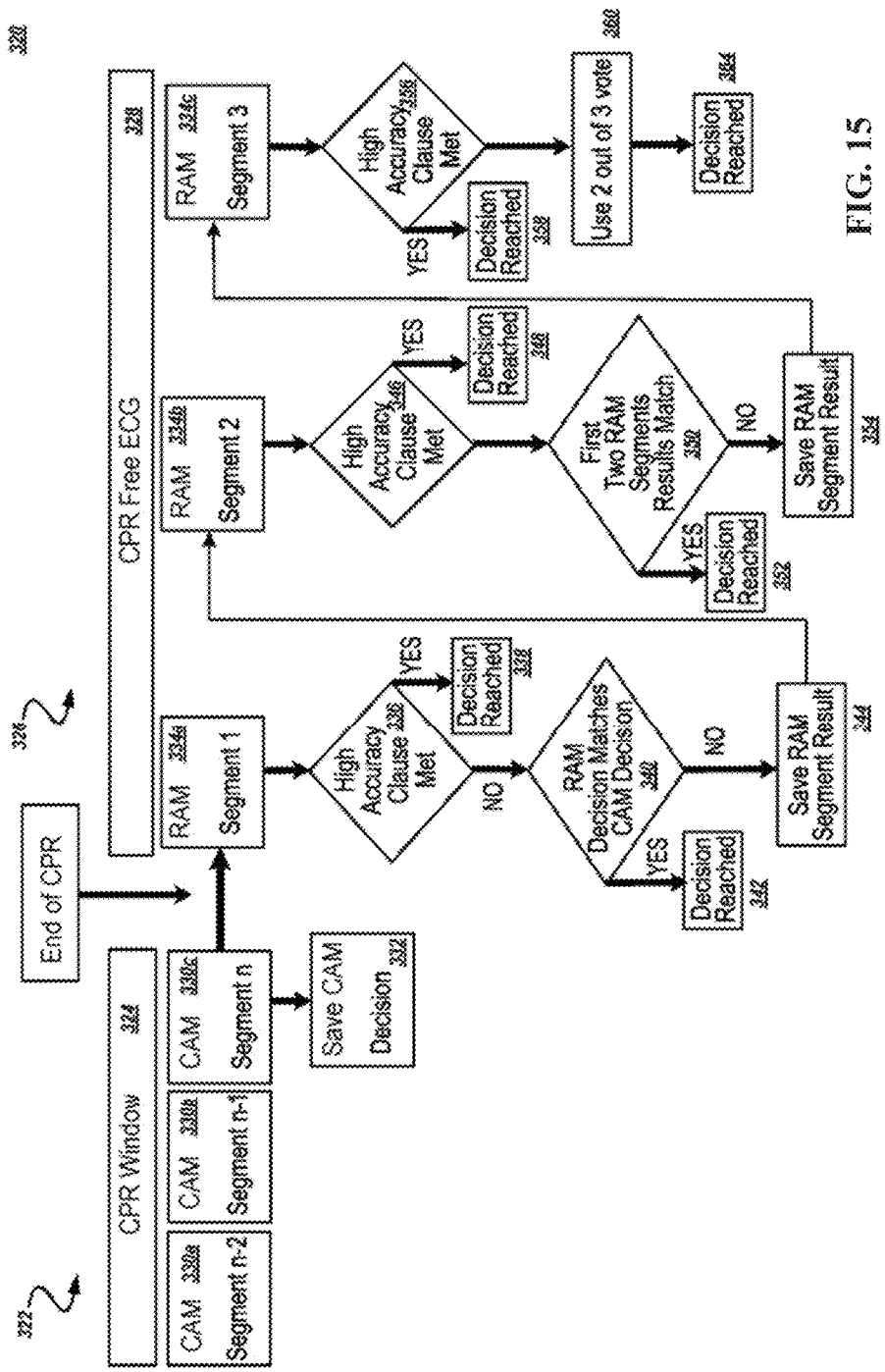
FIG. 15 shows an example schematic for identifying a presence of a shockable rhythm in ECG data.

With reference to FIG. 15, a specific example of a reconfirmation mode is provided. FIG. 15 provides a diagram representing a technique 320 for determining whether a patient is in a shockable or non-shockable state based on an ECG signal measured from the patient, according to either a voting process or whether a high accuracy clause is met before the voting process is complete. As described above, a high accuracy clause is a clause that exhibits a high predictive certainty based on PPV (positive predictable values) and/or NPV (negative predictive value). The technique 320 can be implemented as functionality of a defibrillator, e.g., the AED 10 shown in FIG. 1A.

The technique 320 includes two modes. The first mode 322, which is an optional mode, sometimes referred to as "Continuous Analysis Mode" (CAM), includes a CPR window 324 in which measurements are taken while CPR (chest compressions) is being applied to the victim. During the CAM mode, it may be determined based on the ECG analysis that the patient may or may not require a defibrillation shock, where such a determination is to be confirmed by a hands-free period of ECG analysis. The second mode 326, sometimes referred to as "Reconfirmation Analysis Mode" (RAM), is performed during a CPR-free window 328, e.g., during which time CPR (chest compressions) is not applied to the victim. During the RAM mode, the initial determination made during the CAM mode is confirmed or not confirmed. In some examples, the second mode 326 is entered into once the proximity detector sends a signal to the AED 10 that the rescuer has removed his/her hands from the patient's chest. In some examples, the application of CPR can interfere with detecting a "clean" ECG signal (e.g., a signal absent substantial noise induced by the CPR treatment), so the second mode 326 can be used to detect a CPR-free signal. The technique 320 can alternate between the first mode 322 and the second mode 326, e.g., during a rescue situation. In some examples, the mode changes when the AED 10 detects that CPR has stopped or started (e.g., by detecting that the motion associated with chest compressions has stopped or started or through the use of the proximity detector). In some examples, the mode changes when the AED 10 provides an instruction to a rescuer (e.g., using an output device such as a display or audio output device) to stop or start CPR.

In the first mode 322, an analysis of successive segments 330 a-c of an ECG signal during CPR can be performed. For example, if any clauses used for ECG analysis during CPR are met by any of the segments 330a-c, a decision (e.g., CAM decision) of whether the ECG signal represents a shockable or non-shockable rhythm is saved 332 (e.g., for later comparison with an analysis during the CPR-free window to finalize the determination). The decision can be based, for example, on clauses applied to the segments 330 a-c. Because analysis during CPR may be less reliable than analysis made when CPR has stopped, the saved decision can be confirmed in the second mode 326.

In the second mode 326, CPR is halted and, based on a signal from the proximity sensor, ECG signal segments 334 a-c can be analyzed absent any potential noise from the CPR treatment. A first segment 334a is analyzed, e.g., by applying 336 high accuracy clauses to the segment 334 a. If the high accuracy clause is met, e.g., by indicating a shockable or non-shockable rhythm, then a decision of a shockable or non-shockable rhythm has been reached 338 and further analysis need not be undertaken. If not, other normal accuracy clauses can be applied 340 to the segment 334 a. If one of the other clauses (e.g., a normal accuracy clause) is satisfied by the segment and that clause indicates the same result (e.g., a RAM decision indicating a shockable rhythm or non-shockable rhythm) as was indicated in the saved decision 332 (e.g., CAM decision) of the first mode 322, then a decision of a shockable or non-shockable rhythm has been reached 342. Put another way, because the results match, the matching result (e.g., between the CAM decision and the RAM decision) can be used as the final decision. However, if the other normal accuracy clause(s) indicate a different result as the saved decision, then the result of the other normal accuracy clause(s) is saved 344 and the technique 320 proceeds to analysis of a second segment 334b.

During analysis of the second segment 334b, high accuracy clauses can again be applied 346. If a high accuracy clause is met, e.g., by indicating a shockable or non-shockable rhythm, then a decision of a shockable or non-shockable rhythm has been reached 348 without further processing required. If not, other clauses can be applied 350 to the segment 334 *b*. If another clause (e.g., a normal accuracy clause) indicates the same result (e.g., a shockable rhythm or non-shockable rhythm) as the saved result 344 of the analysis of the first segment 334 *a*, then a decision of a shockable or non-shockable rhythm has been reached 352. If the other normal accuracy clause(s) indicate a different result as the saved result 344, then the result of the other normal accuracy clause(s) is saved 354 and the technique 320 proceeds to analysis of a third segment 334*c*.

During analysis of the third segment 334*c*, high accuracy clauses are again applied 356. If a high accuracy clause is met, e.g., by indicating a shockable or non-shockable rhythm, then a decision of a shockable or non-shockable rhythm has been reached 358. If not, other normal accuracy clauses can be applied 360 to the segment 334*c*, and a "2 out of 3" vote can occur. If another clause (e.g., a normal accuracy clause) indicates the same result (e.g., a shockable rhythm or non-shockable rhythm) as either of the saved result 344 of the analysis of the first segment 334 *a* or the saved result 354 of the analysis of the second segment 334*b*, then a decision of a shockable or non-shockable rhythm has been reached 364. Put another way, when two of the three results match, those matching results (e.g., shockable or non-shockable) is used as the decision of whether the patient is in a shockable or non-shockable state. Additional examples of reconfirmation analysis are provided in United States Patent Application Publication No. 2017/0225001, which is hereby incorporated by reference.

Figure 16:
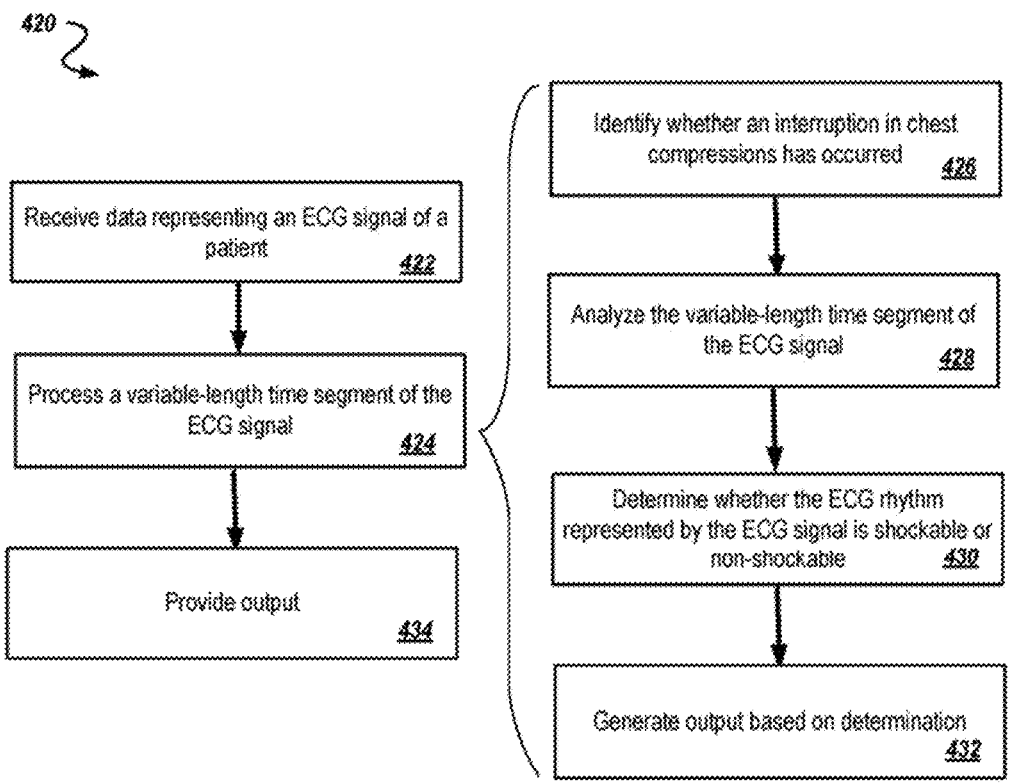
FIG. 16 shows a flowchart of an example processes for identifying a presence of a shockable rhythm in ECG data.

FIG. 16 shows a flowchart of an example process 420 for identifying a presence of a shockable rhythm in ECG data. The process 420 can be implemented, for example, by the MPU 212 shown in FIG. 12, and applied to ECG data.

The process 420 includes receiving 422 data representing an ECG signal of a patient e.g., while the patient is undergoing rescue treatment. The process 420 includes processing 424 a variable-length time segment of the ECG signal comprising an initial time period of between 0.1 second and approximately 3 seconds. The processing includes identifying 426 whether an interruption in chest compressions has occurred, e.g., by processing signals produced from at least one of an ECG electrode and a motion sensor. The processing includes analyzing 428 the variable-length time segment of the ECG signal during the chest compression interruption according to an initial rule set based on the initial time period. The analysis can be used to determine whether an ECG rhythm represented by the ECG signal is shockable or non-shockable. In some examples, the initial rule set includes one or more clauses representing constraints on one or more features of the ECG signal, each of the one or more features of the ECG signal representing a characteristic of a waveform of the ECG signal within the processed time segment.

The processing includes, based on the initial rule set, determining 430 whether the ECG rhythm represented by the ECG signal is shockable or non-shockable or whether to extend the variable-length time segment for further analysis (e.g., if no accurate determination can be made using the initial time period). The processing includes generating 432 an output based on the determination of whether the ECG rhythm represented by the ECG signal is shockable or non-shockable. The process 420 includes providing 434 an output based on the determination, e.g., by using an output circuit or output module (e.g., output screen, audio circuit, etc.).

As discussed herein, in the interest of determining whether an ECG rhythm represented by an ECG signal is shockable or non-shockable as quickly as possible, it may be desirable for gaps or interruptions in chest compressions to be analyzed as quickly and efficiently as possible. Accordingly, the use of a proximity detector to determine the exact moment in which the rescuer removes his/her hands from the patient's chest is beneficial. At any point whenever chest compressions have ceased, even for a short period, an ECG analysis to determine whether a rhythm is shockable or non-shockable, or to determine if more time is needed, may be appropriate. In some instances, interruptions in chest compressions may be fairly short (e.g., less than approximately 3 seconds). For instance, the rescuer may be inclined to readjust his/her position, switch roles with another rescuer, be distracted, slightly fatigued or may otherwise pause chest compressions. For such cases, since it is indeterminate as to when chest compression will recommence, it may be advantageous for the system to begin its rhythm analysis immediately, so that minimal time for determining the cardiac state of the patient is wasted. In some instances, the time period of chest compression interruption may be substantial (e.g., greater than 12-15 seconds). For example, the rescuer may be instructed to stop CPR chest compressions and wait for the defibrillating system to perform an ECG analysis, the rescuer may switch to another resuscitation activity altogether, such as ventilation, etc. In such cases, the ECG analysis may run its regular course.

For various implementations, as discussed above, the defibrillator system may be configured to begin ECG analysis as soon as it identifies an interruption in chest compressions being administered to the patient, or shortly thereafter. The defibrillator system may track chest compressions by any suitable method or technique. In some implementations, the defibrillator system incorporates a motion sensor (e.g., accelerometer, velocity sensor, displacement sensor) at a location where the rescuer is administering chest compressions, to detect the presence of the chest compressions. For example, an accelerometer may be embedded in a chest compression sensor and the rescuer may place the chest compression sensor between the patient's chest and his/her hands during CPR compressions. The acceleration signals produced by the sensor may be processed accordingly. Such a motion sensor may further be used to sense the depth and rate of chest compressions, so as to provide the rescuer with appropriate CPR feedback. Various implementations where a determination of whether a cardiac rhythm is shockable based only on time periods of the ECG signal during which there has not been CPR chest compressions delivered are described in U.S. Pat. No. 6,961,612, entitled "CPR Sensitive ECG Analysis in an Automatic External Defibrillator," which is hereby incorporated by reference in its entirety, and may be used in conjunction with systems and methods described herein. Alternatively, or in addition to such a motion detector, a proximity detector positioned at a location on a patient's chest at which chest compressions will be delivered can be utilized to identify when chest compressions have ceased.

FIGS. 17A-17F depict illustrative implementations that include schematics where the defibrillator system quickly identifies whether an interruption in chest compressions has occurred and applies an appropriate analysis algorithm. In each implementation, the respective schematics show a period of time in which CPR chest compressions are being provided. During this CPR window, as described further herein, the defibrillator system may optionally apply a continuous analysis advisory for whether a shockable or non-shockable rhythm is detected, while taking into account artifacts that arise through chest compressions. Such a continuous analysis advisory may include appropriate filtering, frequency-based analyses, and/or other suitable analysis techniques for providing an indication of whether a rhythm represented by the ECG signal is shockable or non-shockable. This indication may be used to make a determination (subsequently or at the time of analysis) of whether a defibrillating shock should be applied. For example, the continuous analysis advisory may indicate that the ECG rhythm is likely to be shockable, and such an indication may be subsequently confirmed via a subsequent hands-free ECG analysis, where CPR chest compressions are not occurring. In general, a hands-free ECG analysis may provide more accurate shock analysis than continuous ECG analysis during compressions. Examples of suitable continuous analysis advisory algorithms (while during compressions) that may be employed include those described in U.S. Pat. No. 8,706,214, entitled "ECG Rhythm Advisory Method," and U.S. Pat. No. 8,880,166, entitled "Defibrillator Display," each of which are hereby incorporated by reference in their entirety.

As discussed above, to make a final determination of whether the ECG rhythm sensed from the patient is one where a defibrillating shock should be applied, it may be necessary to stop chest compressions for a brief period to analyze a more clean ECG (e.g., without artifacts arising from CPR chest compression). Accordingly, the defibrillating system may prompt the user to stop CPR, for example, via an audio and/or visual prompting from the user interface of the defibrillator. If the user acknowledges this prompting and interrupts the process of applying CPR chest compressions, the system will then analyze the clean ECG (absent chest compressions) to determine whether a shockable or non-shockable rhythm exists when the proximity detector provides sufficient information to confirm a determination that the hands of the rescuer have been removed from the patient's chest. However, the user might not acknowledge the prompt to stop CPR (e.g., might not see/hear, or may ignore the prompting from the defibrillator) and continue chest compressions. If the user continues chest compressions, despite the prompting to stop chest compressions, the system may continue to apply the continuous analysis advisory that takes into account chest compression artifacts in the ECG. Though, once the user halts chest compressions, the system may immediately or within a short period of time switch the type of ECG analysis from the continuous analysis advisory (with compressions) to a hands-free analysis mode (without compressions), which is able to more accurately confirm whether a shockable or non-shockable rhythm exists.

Figure 17A:
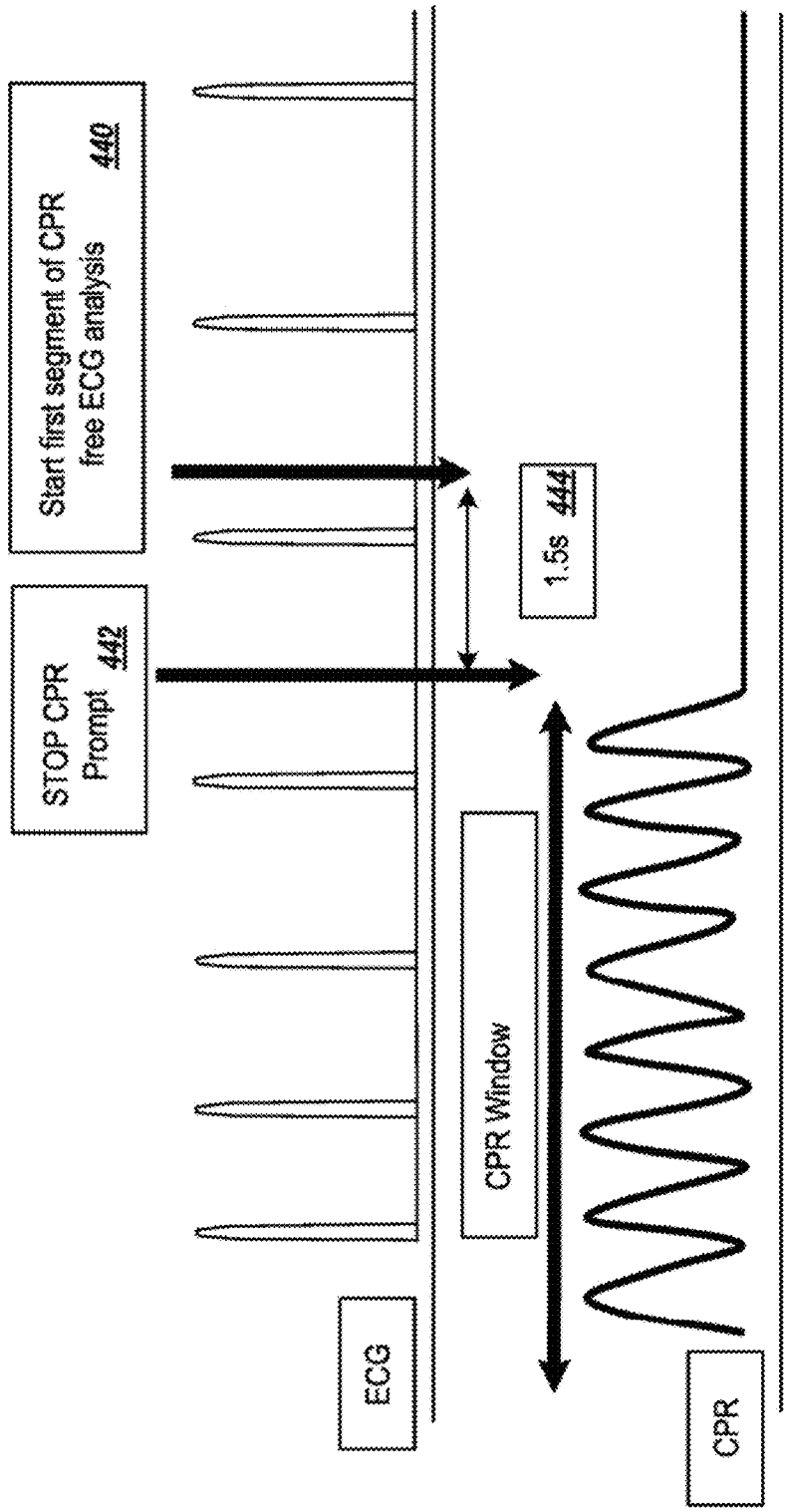
FIGS. 17A-17F show examples of ECG waveforms in relation to CPR treatments.

As shown in FIG. 17A, when the defibrillator system determines that chest compressions should cease in favor of analyzing 440 the ECG signal to determine whether a shock should be applied, an instructive prompt 442 is issued for the rescuer to stop CPR and be hands-free from the patient. In various implementations, the system may optionally pause for a short period of time before hands-free ECG analysis. This short pause 444 may be preferable in some cases to ensure that the ECG signal is substantially free of artifact, present or residual, having arisen from the chest compressions. In some embodiments, a proximity sensor or detector may be used during this short pause 444 to confirm that compressions are not being provided to the patient. While the example of FIG. 17A shows the short pause time before hands-free ECG analysis to be approximately 1.5 seconds, any appropriate pause time may be employed, such as less than 2 seconds, less than 1.5 seconds, less than 1 second, less than 0.5 seconds, less than 0.2 seconds, less than 0.1 second, etc. In some implementations, while not shown in this figure, upon detection of an interruption in chest compressions, the hands-free ECG analysis advisory may be immediately employed.

Figure 17B:
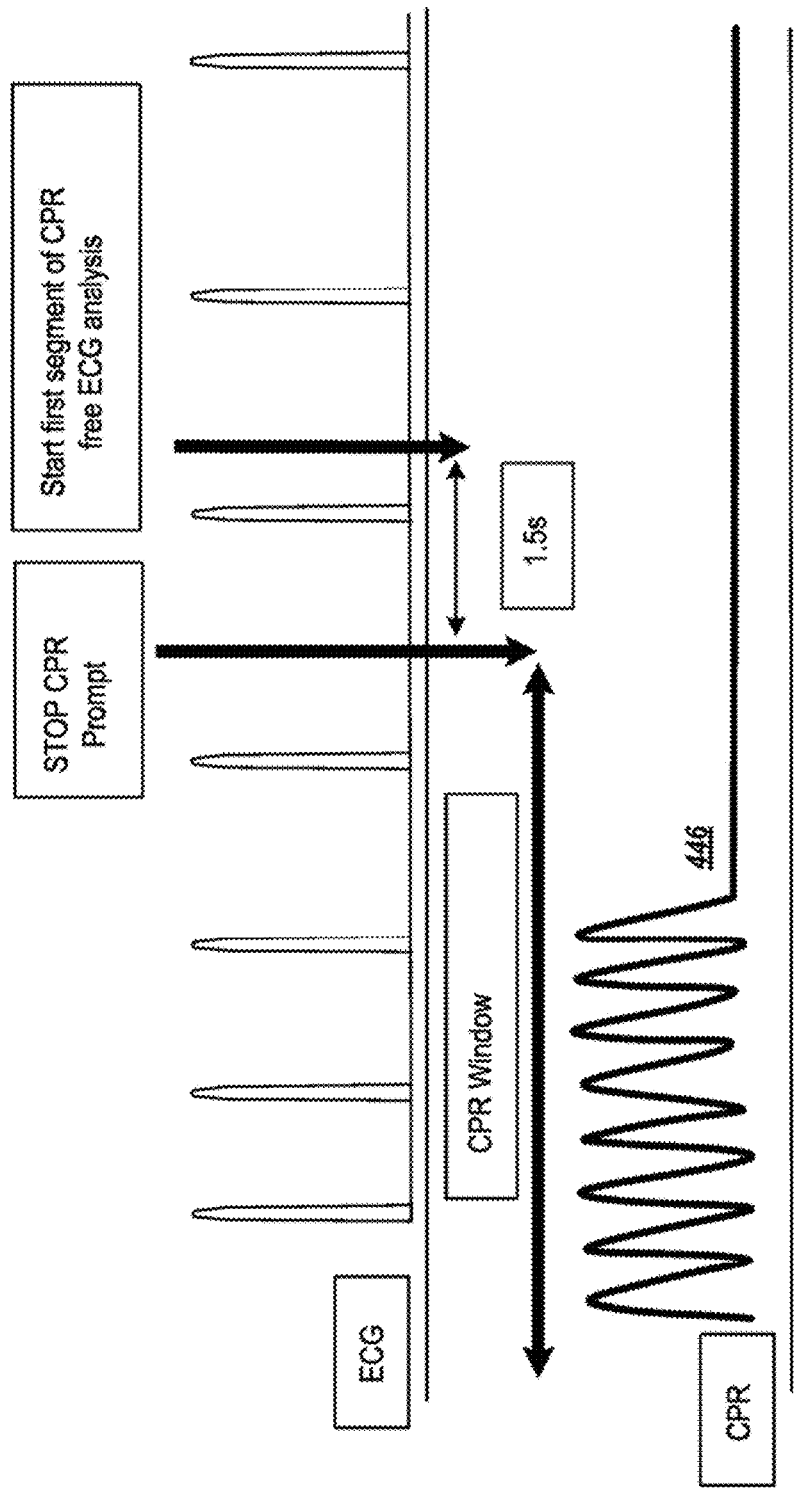

FIG. 17B depicts an implementation where chest compressions are stopped 446 even prior to when the instructive prompt is provided by the system. While it is not advisable to cease chest compressions prematurely, for various reasons, it is common for rescuers to do so. In such a case, while not shown in the figure, the system may prompt the rescuer to continue chest compressions or display an idle timer that shows how long the rescuer has ceased compressions, up until the time when the system determines that chest compressions should be interrupted for hands-free analysis to commence. The implementation of FIG. 17B still pauses for a short period of time after the prompt to stop CPR, however, it can be appreciated that such a pause is not required. For example, when an interruption in chest compressions is detected via information generated by the proximity detector, for example, the system may automatically and/or immediately begin hands-free ECG analysis advisory without any such pause.

Figure 17C:
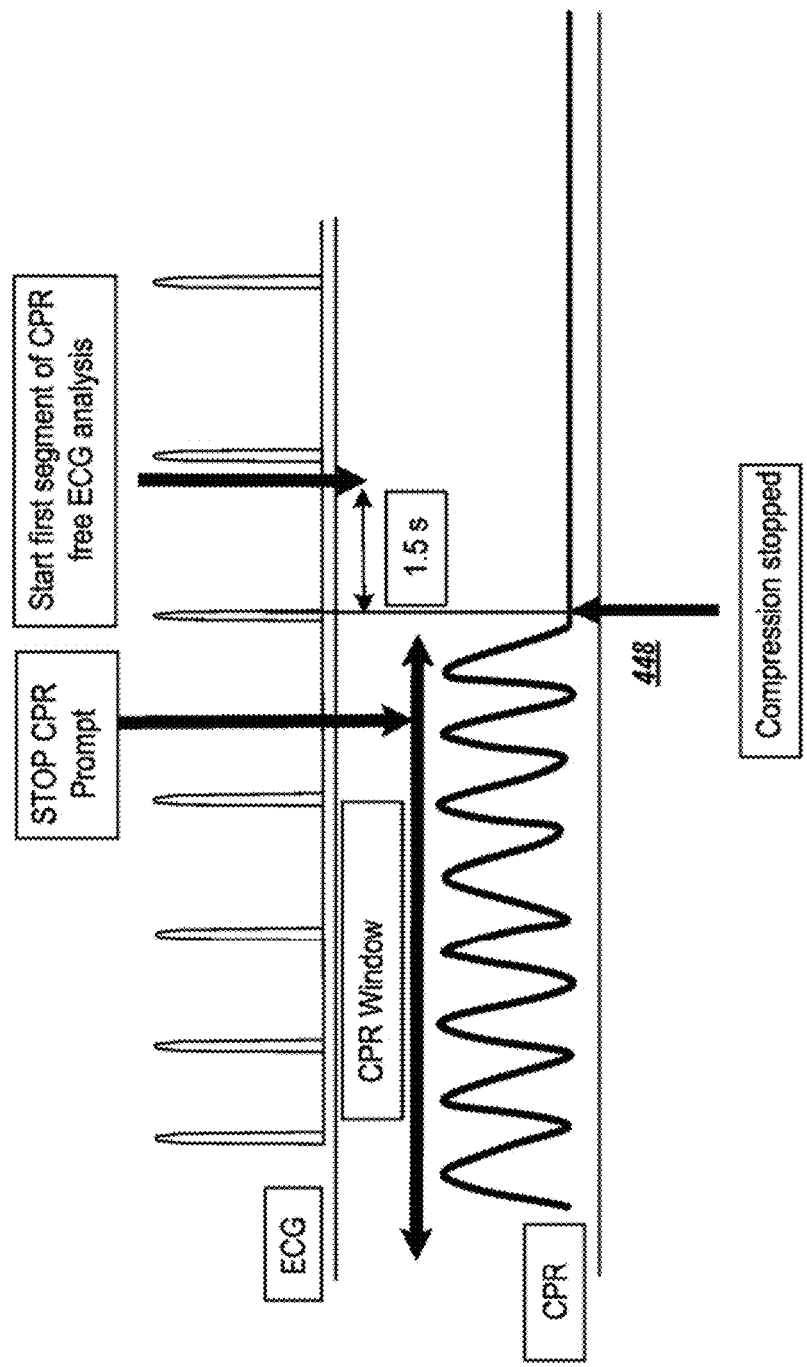

FIG. 17C shows an implementation where chest compressions are continued for a short time 448 (e.g., 1-2 seconds) beyond the time in which the system issues the instructive prompt to stop CPR. In this case, the system tracks the chest compressions up until the time when compressions are ceased, optionally pauses for a short period of time (e.g., approximately 1.5 seconds), and then begins hands-free ECG analysis advisory in accordance with the present disclosure. As discussed above, the short pause in chest compressions may be confirmed using the proximity sensor/detector.

Figure 17D:
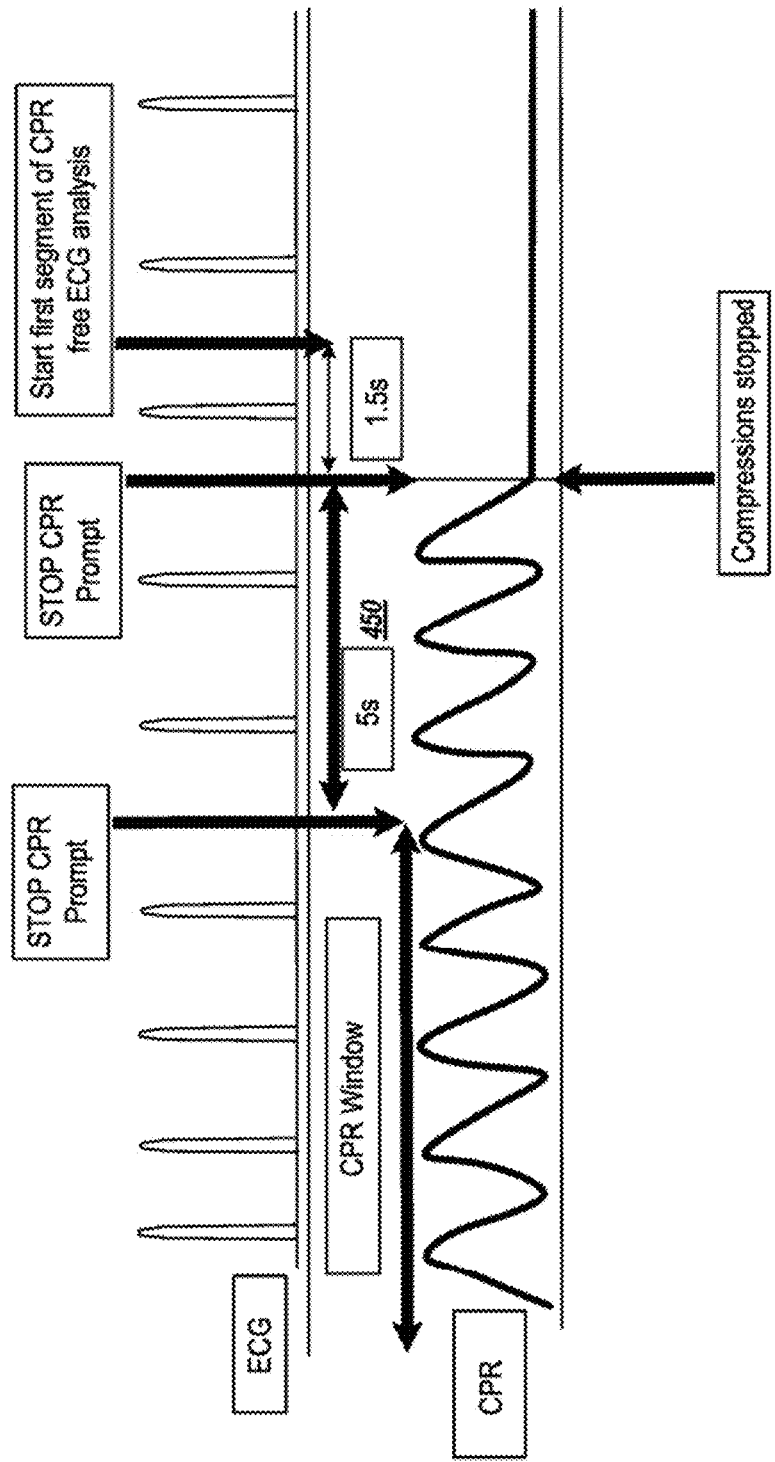

FIG. 17D depicts another implementation of an instance where chest compressions are continued for a longer period 450 than that shown in FIG. 17C. Here, the system continues to track the chest compressions, and after a sufficiently long time period, the system then issues a subsequent instructive prompt reminding the rescuer to stop CPR. It can be appreciated that the subsequent instructive prompt can be provided at any suitable time, which may be predetermined by an appropriate time interval. In this particular case, the system issues the subsequent prompt after approximately 3 seconds which, in some cases, may be similar to an initial time period of ECG analysis. As further shown, when chest compressions are interrupted, the system optionally pauses for a short time (e.g., approximately 1.5 seconds) when it is confirmed that the hands are off the chest, and then commences hands-free ECG analysis advisory.

Figure 17E:
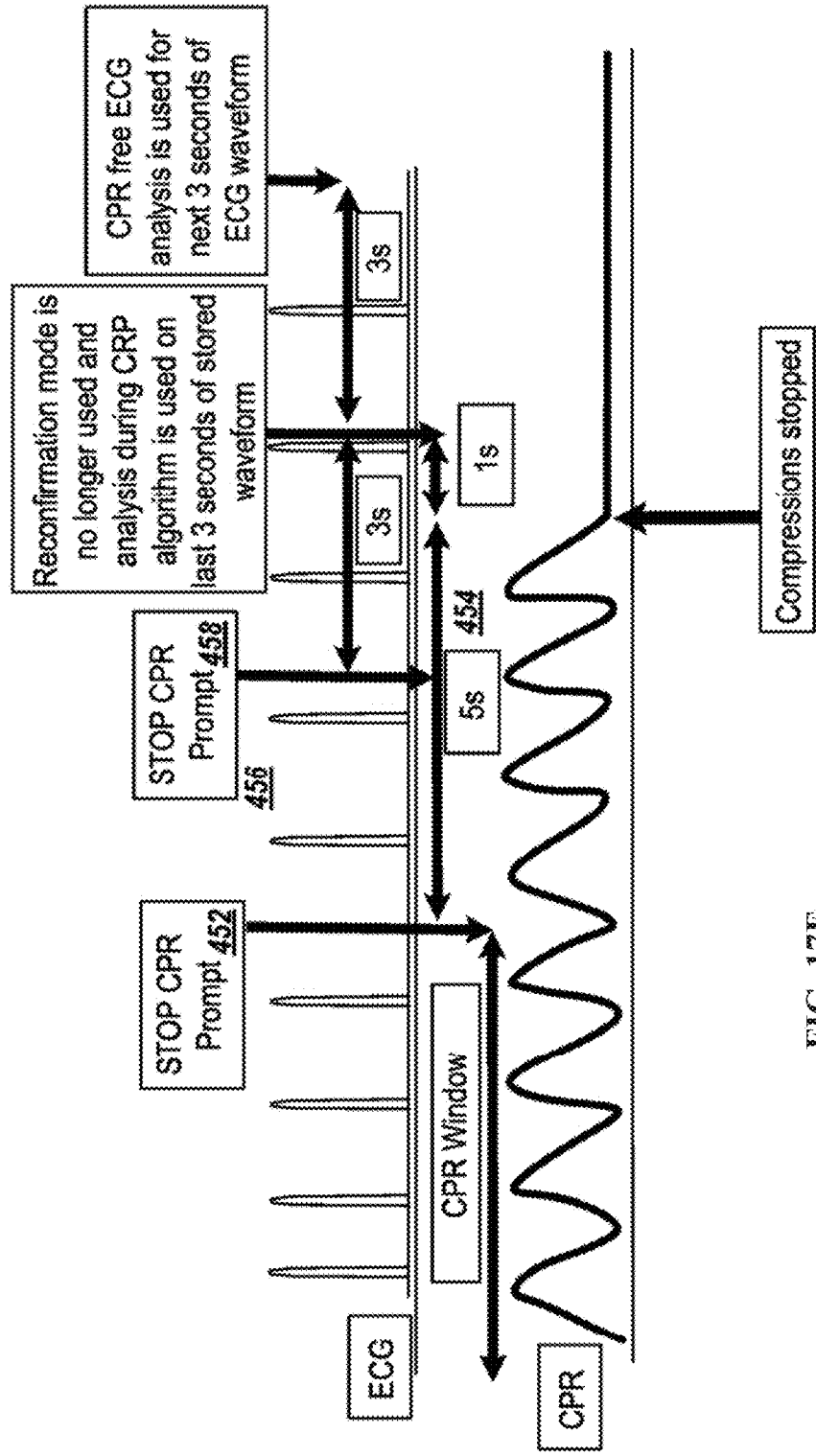

FIG. 17E shows an implementation where chest compressions are continued for an even longer period of time 452. In this example, the system issues the first prompt 454 instructing the user to stop chest compressions, and then after a sufficiently long time interval 456 (e.g., approximately 3 seconds), the system then issues a subsequent instructive prompt 458 reminding the rescuer to stop CPR compressions. However, here, the system continues to sense chest compressions after the subsequent instructive prompt, resulting in further delay in the hands-free CPR analysis advisory. In various implementations, the ECG signal is tracked according to short time segments (e.g., approximately 3 seconds), and once the system identifies an interruption in chest compressions, the hands-free CPR analysis advisory begins at the start of the next time segment. As shown more specifically in FIG. 17E, the system does not detect an interruption in chest compressions, for example, via information generated from the proximity sensor/detector, until approximately 2 seconds after the most recent instructive prompt to stop CPR compressions. The hands-free CPR analysis advisory then begins after the approximately 1 second that remains in the 3 second interval elapses. Though, for certain implementations, after the subsequent instructive prompt, as soon as an interruption in chest compressions has been determined, the system may immediately begin hands-free CPR analysis advisory, without the optional pause.

Figure 17F:
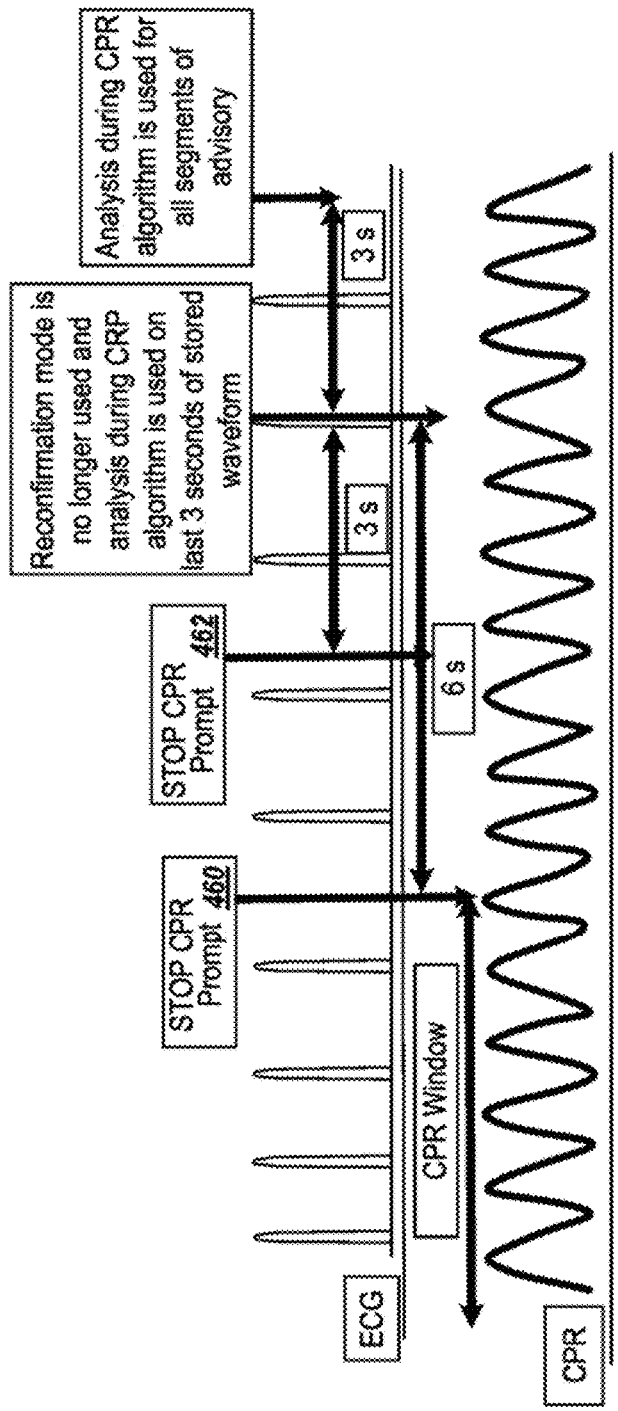

FIG. 17F depicts another illustrative implementation where no interruption in CPR chest compressions is detected, despite multiple instructive prompts 460, 462 to stop chest compressions. In such a case, because chest compressions remain uninterrupted, for example, as determined via the proximity sensor/detector, the hands-free CPR analysis advisory is unable to be used. In this case, the continuous analysis advisory algorithm (which accounts for chest compression artifacts) is applied throughout the time in which chest compressions are administered.

B. Defibrillator Charging

The AED 10 also includes a charging module, such as the defibrillator pulse generator 24, that is configured to charge the AED. In some implementations the AED 10 can be adaptively charged based on monitored ECG signals. For example, the defibrillator can be pre-charged only if a shockable rhythm is likely to exist as determined by analysis of the monitored ECG signals. In another example, the level of charge for the device can be determined and set based on the monitored ECG signals. In some implementations, the method of charging (e.g., the rate of charge, time of charging relative to the resuscitation process) can be varied based on the monitored ECG signals in an effort to conserve power. For example, if time allows, a capacitor may be charged more slowly than it normally would in order to conserve power, but still ensure that the capacitor will reach its full charge just as the defibrillator is needed by the rescuer. An early identification of shockable rhythms, as may be facilitated by the technology described herein, may be used in determining the method of charging. For example, a fast charging process can be triggered upon identification of a shockable rhythm, thereby further reducing potentially life-threatening delays in administering a shock. On the other hand, if a shockable rhythm is not detected, the AED 10 can be charged more slowly in order to achieve power savings. Or, if it appears that an ECG rhythm may be shockable, but is not yet confirmed, the defibrillator may preemptively begin charging in case the rhythm does turn out to be shockable. This feature may be useful when ECG analysis occurs during chest compressions or during reconfirmation mode, where a short time period of analysis after chest compressions is used to confirm the existence of a shockable rhythm that had been detected during chest compressions. In such a case, the defibrillator may begin charging during the administration of chest compressions so that the defibrillator is readily able to deliver a shock once the presence of a shockable rhythm is confirmed. Alternatively, the defibrillator may begin charging based on a signal from the proximity sensor indicating that the rescuer has ceased chest compressions, for example, during the reconfirmation period. Further details of defibrillator charging are described in United States Patent Application Publication Nos. 2016/0220833 and 2017/0225001, which are hereby incorporated by reference in their entirety.

C. Calculating AMSA During Chest Compression Pauses

Changes or trends in spectral frequency (e.g., amplitude spectral area (AMSA), FFT) may be used in evaluating the likelihood that an electrical shock will lead to a successful therapeutic result (e.g., defibrillation). For example, when the AMSA or other frequency-based data is greater than a certain threshold, the percentage of shock success can be sufficiently high such that a caregiver or medical apparatus can make a decision to administer an electrical shock. Alternatively, for relatively low values of AMSA or other frequency-based data, observed changes in frequency-based data can be a substantial contributor to the overall percentage of shock success. Changes or trends in spectral frequency of an ECG can provide further information (in addition to the actual values of the spectral frequency analysis), which can beneficially lead to a therapeutic shock at an earlier time, for example, as compared to a case where only the actual values of the spectral frequency are taken into account. Accordingly, by implementing systems and methods described herein, patients can be able to receive life-saving therapies quickly and effectively. However, AMSA calculations used to predict the likelihood of shock success are much more reliable during pauses in chest compressions. Therefore, a proximity sensor may be utilized to detect when the hands of the rescuer have been removed from the patient's chest such that AMSA or other frequency-based data may be calculated, and the likelihood of shock success may be more reliably determined.

Figure 18:
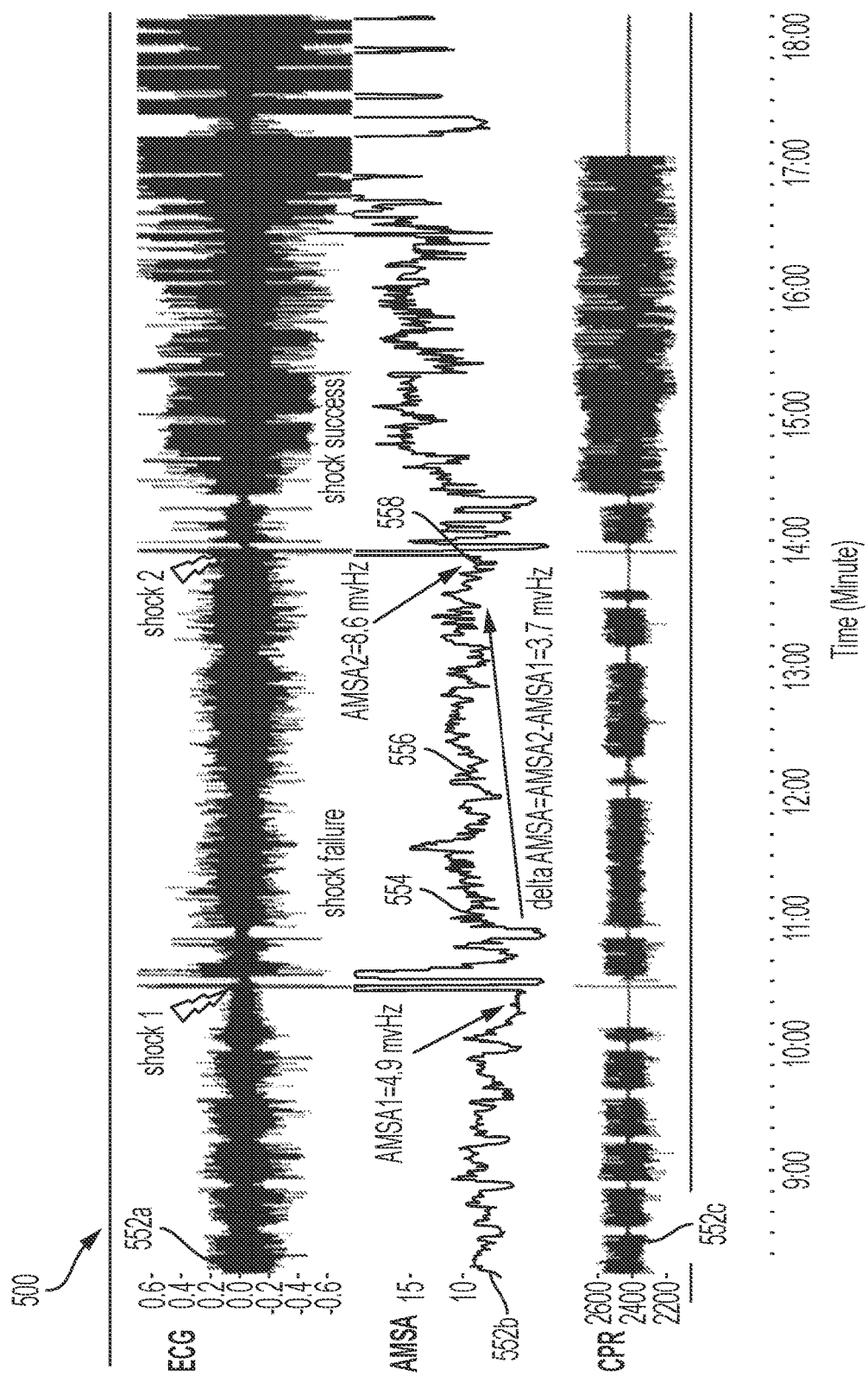
FIG. 18 is an example display including ECG, AMSA, and CPR representations.

With reference to FIG. 18, an example of where AMSA calculations were made during pauses in chest compressions are illustrated. As discussed above, the pauses in chest compressions may be determined through the use of a proximity sensor positioned at or nearby a location on the patient's chest where chest compressions are delivered. More specifically, FIG. 18 is an example of a graphical representation 500 that can be displayed by a patient monitoring and/or treatment device. The example graphical representation 500 includes a parallel display of an ECG signal 552*a*, AMSA 552*b*, corresponding to the ECG signal, and a CPR signal 552*c*, recorded in parallel with the ECG signal. Line 552*b* is represented as AMSA values computed periodically throughout the allotted time period, including during cardiac treatment (e.g., CPR).

The example graphical representation 500 illustrates AMSA 552*b* in a patient suffering of VF, being treated with CPR according to standard protocol (e.g., completing 2 minutes of CPR between each single defibrillation attempt). In the illustrated example, two defibrillation shocks were delivered to the patient. The first shock, which failed, was delivered at around 10 minutes and the second shock, which succeeded, was delivered at around 13 minutes. The average AMSA value measured over a period of few seconds prior to the first shock ($AMSA_1$) was about 4.9 mVHz, which is below an early shock threshold, such as approximately 12 mVHz, approximately 13 mVHz, approximately 14 mVHz, approximately 15 mVHz, or another threshold value. The average AMSA value 158 measured over a period of few seconds prior to the second shock ($AMSA_2$) was about 8.6 mVHz. The general trend of AMSA 552*b* over time illustrates a generally increasing trend between $AMSA_1$ and $AMSA_2$, notably during CPR pauses. Accordingly, it is advantageous to determine such CPR pauses using a proximity detector such that useful values of AMSA can be reliably determined.

In this example, three points on the AMSA line 552*b* are particularly relevant, corresponding to certain evaluation periods: points 554, 556 and 558, which were calculated during CPR pauses to avoid compression artifacts. In one example, the CPR pauses were detected using a proximity sensor as described hereinabove. These points represent evaluation periods at which the combined AMSA value measurement (e.g., mean or median value determined over a window of time) are below a predetermined value associated with defibrillation success, but the change from the first recorded AMSA value $AMSA_1$ (4.9 mVHz) to each of these three points can be used as indicators of defibrillation success. For example, referring to point 556 (taken at a time when there is a pause in CPR compressions, which can generally provide for more reliable AMSA values than when CPR compressions are being administered), the respective AMSA value is about 9 mVHz, which corresponds to a change in AMSA of approximately over 4 mVHz. Such a change in AMSA is indicative of a relatively high likelihood of shock success, at least comparable or greater than the AMSA value at point 558. Such data can indicate that analyzing AMSA in parallel with or in between CPR signals can assist a rescuer in providing successful defibrillation therapy at time intervals different than the standard protocol, defining a personalized treatment optimized for each patient, which can be materially different for different patients. For instance, as shown above, because the change in AMSA from the first recorded AMSA value $AMSA_1$ to point 556 is substantial, the system can provide a recommendation and/or decision for the patient to be treated with an electrical shock at a time (e.g., point 556) prior to the standard treatment protocol, rather than withholding shock treatment until point 558.

If AMSA value is below the predetermined defibrillation threshold (e.g., 15 mVHz) AMSA value can be continuously monitored and the change in AMSA between times $t_1$ and $t_0$ or $t_2$ and can be used to determine when and if a defibrillation shock can be delivered. For a majority of patients with low initial AMSA (as illustrated in FIG. 18), CPR cannot be able to generate an increase of AMSA to reach the early shock threshold, such as approximately 12 mVHz, approximately 13 mVHz, approximately 14 mVHz, approximately 15 mVHz, or another threshold value. In some implementations, an upward overall trend (e.g., linear, non-linear, average increase over time) in AMSA can be used as an indicator that defibrillation can be successful. For example, an absolute change in AMSA determined as the difference between an initial AMSA value and a later AMSA value can be calculated. The change in AMSA value over time can be used in determining a probability of defibrillation success. In some implementations, each unit increase in AMSA, can be associated to a particular percentage increase of the odds of shock success. The upward trend in AMSA over time can be determined over any suitable time period in which resuscitation and/or therapeutic activities are occurring. In some cases, the upward trend can occur for a short, fleeting period, leading to a short interval of opportunity in which the administration of a shock or other appropriate therapy is likely to be successful, despite a generally downward trend over a longer period. The change in AMSA, and, in particular the identification of an upward trend, can be calculated or otherwise determined via any suitable mathematical method. For example, the change in AMSA can be estimated based on calculating a slope of a line intersecting two or more AMSA points, by using a polynomial function, by implementing a non-linear function, calculating a spline estimation, by determining the derivative, by using regression analysis, by applying interpolation techniques, and/or other methods familiar to those of skill in the art.

In some implementations, a change in AMSA can be a more sensitive indicator for shock success in patients with low initial AMSA and a metric derived from the change in AMSA can be useful to guide CPR efforts, including timing of shock delivery. In some implementations, a table or an odds ratio-AMSA range curve can be used to directly identify the increase in defibrillation success for each mVHz change in AMSA. Additional details of the manner in which changes or trends in spectral frequency (e.g., AMSA, FFT) can be used in evaluating the likelihood that an electrical shock will lead to a successful therapeutic result (e.g., defibrillation) are discussed in United States Patent Application Publication No. 2017/0120063, which is hereby incorporated by reference in its entirety. Based on the above description, it is important to determine a pause in chest compressions prior to calculating AMSA and using the trend to provide an estimation of shock success. Accordingly, the pause in chest compressions can be determined by using a proximity sensor positioned on a patient's chest at a location where chest compressions are delivered. The proximity sensor provides a signal to the defibrillator that the rescuer has removed his/her hands from the chest of the patient. Thereafter, trends over particular time intervals can calculated at the beginning and end of the time interval.

D. Detecting Pauses in Chest Compressions to Provide a Ventilation Indication

In yet another implementation, a proximity sensor may be utilized to determine that the rescuer has removed his/her hands from the patient's chest and that compressions have stopped. Once the defibrillator receives such a signal from the proximity detector, the defibrillator is configured to provide at least one of an audible and/or visual indication to the user to begin ventilations either manually through the use of a bag or by an automated ventilation system.

As an example, a common protocol employed by emergency services during resuscitation is a 30:2 protocol, where 30 chest compressions are applied for every 2 positive ventilation breaths. Thus, the system may provide an indication of the number of chest compressions that have been applied so as to guide/coach the user in applying ventilations at the appropriate time(s), and/or to coordinate timing of positive pressure breaths provided by an automated ventilation system. For example, if a 30:2 compressions to ventilations protocol is employed, the proximity sensor, either alone or in combination with a motion sensor as described hereinabove, may be used to detect whether chest compressions are applied. The system may further count the number of applied compressions and then alert the rescuer to give breaths once the proximity detector issues a signal indicating the chest compressions have ceased.

In some embodiments, it can be beneficial to time the CPR compressions such that the CPR compression does not occur at the same time as a ventilation. In such cases where a positive pressure ventilation and a chest compression are administered simultaneously, the sudden pressure build up within the thoracic cavity may be injurious. Accordingly, the system may time compressions provided by manual CPR compressions via the proximity sensor. Based on information from the proximity sensor, the system determines whether a timing for a ventilation overlaps with a timing for a CPR compression cycle and provides an indication to the rescuer if a ventilation is being delivered during a compression cycle so the rescuer can delay either the compression or the ventilation so that they do not overlap. Or, in some cases, when it is time to prompt the user to administer a positive pressure ventilation, the proximity sensor may be used to confirm that a chest compression is not occurring and then the appropriate prompt to give the positive pressure breath may be given.

Many other implementations other than those described may be employed, and may be encompassed by the following claims.

The invention claimed is:

1. A medical system for providing resuscitative treatment to a patient, the system comprising:
   a compression housing configured to be placed on a sternum of the patient during the resuscitative treatment, the compression housing comprising:
      a motion sensor provided with the compression housing and configured to produce signals representative of motion of the sternum of the patient during chest compressions; and
      a proximity sensor provided with the compression housing and configured to produce signals indicative of whether a rescuer's hands are in contact with the compression housing or not in contact with the compression housing; and
   one or more processors communicatively connected to the motion sensor and the proximity sensor, the one or more processors configured to:
      receive the signals from the motion sensor and the proximity sensor;
      determine whether chest compressions have been initiated based on the signals from the motion sensor and the proximity sensor; and
      provide chest compression feedback based on whether chest compressions have been initiated.

2. The system of claim 1, wherein the proximity sensor comprises at least one of: a capacitive sensor, an ultrasonic sensor, an E-field sensor, and a light emitter-receiver pair.

3. The system of claim 2, wherein the signals from the proximity sensor indicative of whether the rescuer's hands are in contact with the compression housing are generated based on a measurement from the proximity sensor that the rescuer's hands are greater than 1 cm away from the compression housing.

4. The system of claim 1, wherein the processor is provided as a component of a defibrillator.

5. The system of claim 4, wherein the defibrillator comprises a feedback device configured to provide the chest compression feedback.

6. The system of claim 1, wherein the chest compression feedback is at least one of: audio feedback and visual feedback.

7. The system of claim 1, wherein the chest compression feedback comprises displaying on a display screen an indicator that indicates whether the chest compressions are being performed properly.

8. The system of claim 1, wherein the one or more processors are further configured to determine at least one of: a rate of compressions and a depth of compressions, based on the signals from the motion sensor during delivery of the chest compressions.

9. The system of claim 8, wherein the chest compression feedback comprises an indication of: at least one of the rate of compressions and the depth of compressions.

10. The system of claim 1, wherein the one or more processors are further configured to:
    determine whether the rescuer's hands have been fully released from the compression housing based on the signals from the proximity sensor; and
    provide an indication comprising information about whether a rescuer is fully releasing.

11. The system of claim 10, wherein the indication comprising information about whether the rescuer is fully releasing is a release indication icon displayed on a display screen where an amount of fill in the box varies to indicate whether the rescuer is fully releasing between chest compressions.

12. The system of claim 1, wherein the motion sensor comprises at least one of: an accelerometer, a pressure sensor, and a velocity sensor.

13. The system of claim 1, wherein the one or more processors are configured to provide the chest compression feedback based on whether the signals from the proximity sensor indicate that the rescuer's hands are in contact with compression housing.

14. The system of claim 1, wherein the one or more processors are configured to withhold the chest compression feedback based on whether the signals from the proximity sensor indicate that the rescuer's hands are not in contact with compression housing.

15. A method for providing resuscitative treatment to a patient, the method comprising:
    placing a compression housing on a sternum of the patient; the compression housing comprising a proximity sensor and a motion sensor positioned in the compression housing; and
    receiving chest compression feedback when a determination has been made that chest compressions have been initiated based on signals from the motion sensor and the proximity sensor.

16. The method of claim 15, wherein the chest compression feedback is received when the signals from the proximity sensor indicate that the rescuer's hands are in contact with the compression housing.

17. The method of claim 15, wherein the chest compression feedback is prevented from being received when the signals from the proximity sensor indicate that the rescuer's hands are not in contact with the compression housing.

18. The method of claim 15, wherein the chest compression feedback is at least one of: audio feedback and visual feedback.

19. The method of claim 15, wherein the chest compression feedback comprises displaying on a display screen an indicator that indicates whether the chest compressions are being performed properly.

20. The method of claim 15, wherein the chest compression feedback comprises an indication of at least one of a rate of: compressions and a depth of compressions based on the signal from the motion sensor.

* * * * *